US012799191B2

(12) United States Patent
Pandya et al.

(10) Patent No.: US 12,799,191 B2
(45) Date of Patent: Nov. 17, 2026

(54) TREATING ACUTE RESPIRATORY DISTRESS SYNDROME WITH IL-33 AXIS BINDING ANTAGONISTS

(71) Applicant: MEDIMMUNE LIMITED, Cambridge (GB)

(72) Inventors: Hitesh Champaklal Pandya, Cambridge (GB); Emma Suzanne Cohen, Cambridge (GB); Christopher Martin Kell, Cambridge (GB)

(73) Assignee: MedImmune Limited, Cambridge (GB)

( * ) Notice: Subject to any disclaimer, the term of this patent is extended or adjusted under 35 U.S.C. 154(b) by 923 days.

(21) Appl. No.: 17/995,507

(22) PCT Filed: Apr. 1, 2021

(86) PCT No.: PCT/EP2021/058749

§ 371 (c)(1), (2) Date: Oct. 5, 2022

(87) PCT Pub. No.: WO2021/204707

PCT Pub. Date: Oct. 14, 2021

(65) Prior Publication Data

US 2023/0174637 A1 Jun. 8, 2023

Related U.S. Application Data

(60) Provisional application No. 63/140,502, filed on Jan. 22, 2021, provisional application No. 63/015,915, filed on Apr. 27, 2020, provisional application No. 63/005,649, filed on Apr. 6, 2020.

(51) Int. Cl.
*A61P 31/14* (2006.01)
*C07K 16/24* (2006.01)

(52) U.S. Cl.
CPC ............ *C07K 16/244* (2013.01); *A61P 31/14* (2018.01); *C07K 2317/565* (2013.01)

(58) Field of Classification Search
None
See application file for complete search history.

(56) References Cited

U.S. PATENT DOCUMENTS

2018/0155436 A1* 6/2018 Orengo .................. A61P 17/00
2019/0321370 A1 10/2019 Sorrentino et al.

FOREIGN PATENT DOCUMENTS

CN 106198953 A 12/2016
WO 2016/156440 A1 10/2016
WO 2017/187307 A1 11/2017

OTHER PUBLICATIONS

Saguil et al., Am Fam Physician, 2012, 85(4):352-358 (Year: 2012).*
Nin et al., Ann Transl Med 2018, 6(2):37, 6 pages (Year: 2018).*
Hui et al., International Journal of Infectious Diseases, Feb. 2020, Epub Jan. 14, 2020, 91:264-266 (Year: 2020).*
Zizzo and Cohen, Lancet Rheumatol, Dec. 2020, published online Oct. 9, 2020, vol. 2, e779-90 (Year: 2020).*
Huang et al., Lancet, published online Jan. 24, 2020, 395:497-506 (Year: 2020).*
Xiong et al., Emerging Microbes & Infections, published online Mar. 31, 2020, 9(1):761-770 (Year: 2020).*
Allinne et al., "IL-33 blockade affects mediators of persistence and exacerbation in a model of chronic airway inflammation", Journal of Allergy and Clinical Immunology, 2019, vol. 144, No. 6, p. 1624.
Agata et al., "IL-33 Mediated Inflammation in Chronic Respiratory Diseases-Understanding the Role of the Member of IL-1 Superfamily", Frontiers in Immunology, 2019, vol. 10.
Inoue et al., "Combination treatment of short-course systemic corticosteroid and favipiravir in a successfully treated case of critically ill COVID-19 pneumonia with CPOD", Respiratory Medicine CME, 2020.
Wilkinson et al., "Accord: A Multicentre, Seamless, Phase 2 Adaptive Randomisation Platform Study to Assess the Efficacy and Safety of Multiple Candidate Agents for the Treatment of COVID-10 in Hospitalised Patients: A structured summary of a study protocol for a randomized controlled trial", 2020, Trials, vol. 21, No. 1.
Kox, Matthijs, et al., Cytokine Levels in Critically Ill Patients With COVID-19 and Other Conditions, JAMA, vol. 324, No. 15, published online Sep. 3, 2020.
Seeliger, Benjamin et al., Comparison of inflammatory profiles in ARDS due to viral or streptococcal infection vs acute exacerbation of ILD, European Respiratory Journal, 2024 64, (suppl 68): PA810.
Bermudez R M., et al., "Effect of Anti -IL-33 treatment in a Murine Model of Acute Respiratory Distress Syndrome", Intensive Care Medicine Experimental, vol. 7, No. 55, Sep. 27, 2019, pp. 471-473.
Chavez S., et al., "Coronavirus Disease (COVID-19): A Primer for Emergency Physicians", American Journal of Emergency Medicine 44, doi: 10.1016/j.ajem.2020.03.036, PMID: 32265065, PMCID: PMC7102516, pp. 220-229, 2021.
ClinicalTrials.gov: "Proof-of-Concept Study to Assess the Efficacy, Safety and Tolerability of SAR440340 (Anti-IL-33 mAb) in Patients With Moderate-to-severe Chronic Obstructive Pulmonary Disease (COPD)", ClinicalTrials.gov Identifier: NCT03546907, Version 33 (Feb. 27, 2020), last updated Nov. 22, 2022, 21 Pages, available at https://clinicaltrials.gov/study/NCT03546907 (accessed May 21, 2026).
ClinicalTrials.gov: "The Role of IL33/ST2 Axis in ARDS Patients", ClinicalTrials.gov Identifier: NCT02492204, Version 3 (Feb. 24, 2019), last updated Feb. 26, 2019, 8 Pages, available at https://clinicaltrials.gov/study/NCT02492204 (accessed May 20, 2026).
ClinicalTrials.gov: "Study of REGN3500 and Dupilumab in Patients With Asthma", ClinicalTrials.gov Identifier: NCT03112577, Version 6 (Jan. 16, 2020), last updated Jan. 18, 2020, 10 Pages, available at https://clinicaltrials.gov/study/NCT03112577 (accessed May 21, 2026).

(Continued)

*Primary Examiner* — Stacy B Chen
(74) *Attorney, Agent, or Firm* — Arnold & Porter Kaye Scholer LLP

(57) ABSTRACT

The present disclosure is directed to the use of an IL33-axis binding antagonist for the treatment and prevention of acute respiratory distress syndrome (ARDS) and/or symptoms thereof.

13 Claims, 4 Drawing Sheets

Specification includes a Sequence Listing.

(56) References Cited

OTHER PUBLICATIONS

ClinicalTrials.gov: "Study of Safety, Tolerability, and Pharmacokinetics of Multiple Ascending Doses of REGN3500 in Adults With Moderate Asthma", ClinicalTrials.gov Identifier: NCT02999711, Version 6 (Dec. 10, 2018), last updated Dec. 12, 2018, 10 Pages, available at https://clinicaltrials.gov/study/NCT02999711 (accessed May 21, 2026).

International Search Report and Written Opinion for International Application No. PCT/EP2021/058749, dated Jun. 28, 2021, 15 Pages.

Juan F., et al., "Research Progress of Interleukin-33 in Acute Respiratory Distress Syndrome", Journal of Chongqing Medical University, vol. 41, No. 4, Dec. 31, 2016, pp. 425-428.

Lin S.H., et al., "Inflammation Elevated IL-33 Originating from the Lung Mediates Inflammation in Acute Lung Injury," Clinical Immunology, vol. 173, Oct. 29, 2016, pp. 32-43.

Lu R., et al., "Genomic Characterisation and Epidemiology of 2019 Novel Coronavirus: Implications for Virus Origins and Receptor Binding", The Lancet, Feb. 22, 2020, vol. 395, No. 10224, pp. 565-574, DOI: 10.1016/S0140-6736(20)30251-8.

Marraro G.A., et al., "Consideration of the Respiratory Support Strategy of Severe Acute Respiratory Failure Caused by SARS-CoV-2 Infection in Children", Chinese Journal of Contemporary Pediatrics, Mar. 2020, vol. 22, No. 3, pp. 183-194.

Morita H., "The Role of ILC2s in the Pathogenesis of Eosinophilic Airway Inflammation", Allergy, 2019, vol. 68, No. 8, pp. 928-932 (13 Pages).

Nagase H., "The Role of Eosinophils in Allergic Diseases: Insights from Anti-IL-5 Therapy for Asthma", Journal of the Japanese Society of Internal Medicine, 2019, vol. 108, No. 3, p. 587-593.

Nakano Y., et al., "Simultaneous Measurement of Multiple Cytokines by a Bead Array Method in Bronchoalveolar Lavage Fluid of Patients with ALI/ARDS", Artificial Respiration, Oct. 2007, vol. 24, No. 2, pp. 140-145, ISSN: 0910-992.

Shibio W., et al., "Expression and Clinical Significance of IL-33/ST2 Signaling Pathway in Patients with Acute Respiratory Distress Syndrome", Journal of Clinical Emergency(China), vol. 20, No. 4, Dec. 31, 2019, 6 Pages.

Wu C., et al., "Risk Factors Associated With Acute Respiratory Distress Syndrome and Death in Patients With Coronavirus Disease 2019 Pneumonia in Wuhan China", JAMA Internal Medicine, Jul. 2020, vol. 180, No. 7, pp. 934-943.

Zhang Y., et al., "The Role of IL-33 on LPS-Induced Acute Lung Injury in Mice", Inflammation, Nov. 23, 2016, vol. 40, No. 1, 10 pages.

* cited by examiner

TREATING ACUTE RESPIRATORY DISTRESS SYNDROME WITH IL-33 AXIS BINDING ANTAGONISTS

BACKGROUND

Acute respiratory distress syndrome (ARDS) is a life-threatening condition where the lungs cannot provide the body's vital organs with enough oxygen. Characteristic symptoms of ARDS include severe shortness of breath, rapid shallow breathing, tiredness, drowsiness or confusion, and feeling faint. There are many potential causes for ARDS, typically which result in the lungs becoming severely inflamed. Such causes can include pneumonia (viral or bacterial) or severe flu, sepsis, a severe chest injury (e.g. major trauma and/or multiple fractures), aspiration of gastric contents (e.g. accidentally inhaling vomit), smoke or toxic chemicals inhalation, near drowning, pulmonary contusion, fat emboli, pulmonary vasculitis, non-cardiogenic shock or an adverse reaction to a blood transfusion.

Because ARDS is often caused by a serious health condition, the mortality rate is relatively high, although mortality is often linked to the underlying health condition rather than ARDS per se. Nevertheless, providing an effective treatment for ARDS is needed to improve patient outcomes. Providing effective prevention strategies for ARDS may also alleviate strain on health care systems by reducing patient times to discharge and lowering the need for intensive care for patients admitted to primary care facilities. Patients with ARDS often require mechanical intubation or the use of a ventilator to assist with breathing. Fluid and nutrients may also need to be supplied to a patient through a nasogastric tube. Sometimes, patients may remain in hospital for several weeks, or even months, depending on the severity of ARDS and the underlying health condition. For those who survive, long-term complications linked to nerve and muscle damage can persist, which may cause pain and weakness.

As such, novel, effective therapies for the treatment or prevention of ARDS are required.

SUMMARY OF THE DISCLOSURE

Provided herein are methods of treating or preventing acute respiratory distress syndrome (ARDS), in a patient at risk thereof, comprising administering to the patient an effective amount of an IL-33 axis binding antagonist.

In another aspect, the disclosure provides a method of treating hypoxemia in a patient, comprising administering to the patient an effective amount of an IL-33 axis binding antagonist.

In another aspect, the disclosure provides a method of treating severe pulmonary inflammation in a subject, comprising administering to the patient an effective amount of an IL-33 axis binding antagonist.

In another aspect, the disclosure provides a method of treating or preventing coronavirus disease 2019 (COVID-19) in a patient, the method comprising administering to the patient an effective amount of an IL-33 axis binding antagonist.

Also provided herein are methods of preventing or treating acute respiratory insufficiency in a patient, the method comprising administering to the patient an effective amount of an IL-33 axis binding antagonist. In some instances, the method is for the treatment or prevention of acute respiratory insufficiency induced by coronavirus 2 (SARS-CoV-2) infection.

In another aspect, the disclosure provides a method of treating and/or preventing excessive pulmonary inflammation, the method comprising administering to the patient an effective amount of an IL-33 axis binding antagonist In some instances, the IL-33 axis binding antagonist is an antibody or antigen-binding fragment thereof.

In some instances, the antibody, or antigen-binding fragment thereof, is an anti-IL33 antibody, or antigen binding fragment thereof, comprising a VHCDR1 having the sequence of SEQ ID NO: 37, a VHCDR2 having the sequence of SEQ ID NO: 38, a VHCDR3 having the sequence of SEQ ID NO: 39, a VLCDR1 having the sequence of SEQ ID NO: 40, a VLCDR2 having the sequence of SEQ ID NO: 41, and a VLCDR3 having the sequence of SEQ ID NO: 42

In some instances, the VH and VL of the anti-IL-33 antibody or antigen-binding fragment thereof comprise amino acid sequences at least 95%, 90%, or 85% identical to SEQ ID NO: 1 and SEQ ID NO: 19, respectively.

In some instances, the anti-IL-33 antibody or antigen binding fragment thereof, comprises a VH having the sequence of SEQ ID NO: 1 and a VL having the sequence of SEQ ID NO: 19.

In some instances, the anti-IL-33 antibody or antigen binding fragment thereof is selected from a human antibody, a chimeric antibody, and a humanized antibody.

In some instances, the anti-IL-33 antibody or antigen binding fragment thereof is selected from a naturally-occurring antibody, an scFv fragment, a Fab fragment, a F(ab')2 fragment, a minibody, a diabody, a triabody, a tetrabody, and a single chain antibody.

In some instances, the antibody or antigen binding fragment thereof is a monoclonal antibody.

DESCRIPTION OF THE DRAWINGS

The disclosure is described with reference to the following drawings, in which.

DETAILED DESCRIPTION OF THE DISCLOSURE

General Definitions

Figure 1A:
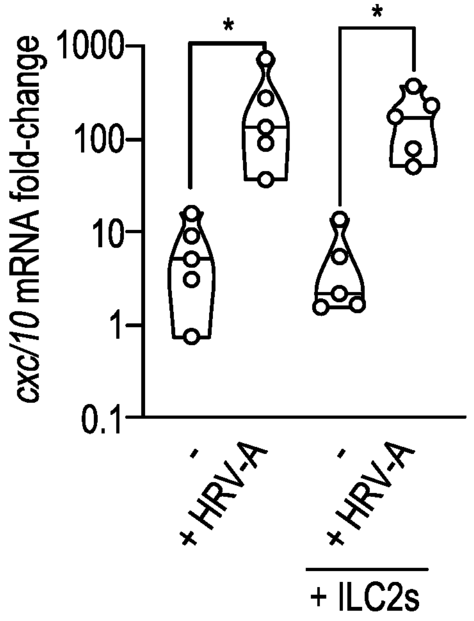
FIG. 1A shows a significant increase in cxcl10 mRNA in ALIs infected HRV-A and incubated alone or with ILC2s for 7 days (Donors n=5).

It is understood that wherever aspects are described herein with the language "comprising," otherwise analogous aspects described in terms of "consisting of" and/or "consisting essentially of" are also provided.

Unless specifically stated or obvious from context, as used herein, the term "or" is understood to be inclusive. The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "about" and "approximately," when used to modify a numeric value or numeric range, indicate that deviations of up to 10% above and down to 10% below the value or range remain within the intended meaning of the recited value or range. It is understood that wherever aspects are described herein with the language "about" or "approximately" a numeric value or range, otherwise analogous aspects referring to the specific numeric value or range (without "about") are also provided.

"Administer," "administering," "administration," and the like refer to methods that may be used to enable delivery of a drug, e.g., an IL-33 axis binding antagonist, e.g., an anti-IL33 antibody, or antigen binding fragment thereof, as described herein. Administration techniques that can be employed with the agents and methods described herein are found in e.g., Goodman and Gilman, The Pharmacological Basis of Therapeutics, current edition, Pergamon; and Remington's, Pharmaceutical Sciences, current edition, Mack Publishing Co., Easton, Pa. In some aspects, the IL-33 axis binding antagonist is administered parenterally, for example, intravenously or subcutaneously.

"Antibody" is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

"Antigen binding fragment" and "binding fragment" refers to a molecule other than an intact antibody that comprises a portion of the intact antibody that binds to the antigen to which the intact antibody binds. Examples of antibody fragments include, but are not limited to, Fv, Fab, Fab', F(ab')2, Fab'-SH, diabodies, triabodies, tetrabodies, linear antibodies, single-chain antibody molecules (e.g., scFv), and multispecific antibodies formed from antigen binding fragments.

"Complementarity determining regions" and "CDRs" are used herein to refer to the amino acid residues of an antibody or antigen-binding fragment that are responsible for antigen binding.

"Hypoxemia" refers to below-normal level of oxygen in blood. More specifically, it is oxygen deficiency in arterial blood. Hypoxemia is usually defined in terms of reduced partial pressure of oxygen (mmHg) in arterial blood, but also in terms of reduced content of oxygen (ml oxygen per dl blood) or percentage saturation of hemoglobin (the oxygen-binding protein within red blood cells) with oxygen. In an acute context, hypoxemia can cause symptoms such as those in respiratory distress.

These include shortness of breath, rapid shallow breathing, chest pain, confusion, headache and rapid heartbeat shortness of breath. Hypoxemia is determined by measuring the oxygen level in a blood sample taken from an artery (arterial blood gas). It can also be estimated by measuring the oxygen saturation of blood using a pulse oximeter. Hypoxemia is categorized as mild, moderate, or severe, based upon the divergence from the normal range. Generally the following definitions apply: mild hypoxemia: $PaO_2$ (patient's partial pressure of oxygen)=60 to 79 mmHg; moderate hypoxemia: PaO2=40 to 59 mmHg and severe hypoxemia: PaO2<40 mmHg. Values under 60 mmHg usually indicate the need for supplemental oxygen.

"Hypercarbia" (also known as hypercapnia) is a condition of abnormally elevated carbon dioxide ($CO_2$) levels in the blood. Hypercapnia may happen in the context of an underlying health condition, and symptoms may relate to this condition or directly to the hypercapnia. Specific symptoms attributable to early hypercapnia are shortness of breath, anxiety, headache, confusion and lethargy. Clinical signs include flushed skin, full pulse, rapid breathing, premature heart beats, muscle twitches, and hand flaps (asterixis). Hypercarbia can be determined by conducting blood gas tests, typically by radial artery puncture. Hypercarbia is generally defined as an arterial blood carbon dioxide level over 45 mmHg (6 kPa). A rapid increase in blood $CO_2$ levels can result in acute hypercarbia, which can lead to multi-organ complications and can develop during severe COPD exacerbations or other forms of respiratory failure where breathing muscles become exhausted, such as during severe pneumonia.

"IL-33" protein as employed herein refers to interleukin 33, in particular a mammalian interleukin-33 protein, for example human protein deposited with UniProt number 095760. This entity is not a single species but instead exists in several forms with different functional activities e.g. full length and proteolytically processed forms or oxidized and reduced forms (Cohen et al, 2015 Nat Comm 6:8327; Scott et al., 2018 Sci Rep 8:3363). Given the rapid oxidation of the reduced form in vivo, and in vitro, generally prior art references to IL-33 might be most relevant to detection of the oxidized form. The terms "IL-33" and "IL-33 polypeptide" and "IL-33 protein" are used interchangeably.

"Interleukin 1 receptor-like 1 (IL 1 RL 1)" and "ST2" are used interchangeably and refer to any native ST2 from any vertebrate source, including mammals such as primates (e.g., humans) and rodents (e.g., mice and rats), unless otherwise indicated. ST2 is also referred to in the art as DER4, T1, and FIT-1. The term encompasses "full-length," unprocessed ST2, as well as any form of ST2 that results from processing in the cell. At least four isoforms of ST2 are known in the art, including soluble (sST2, also known as IL 1 RL 1-a) and transmembrane (ST2L, also known as IL 1 RL 1-b), which arise from differential mRNA expression from a dual promoter system, and ST2V and ST2LV, which arise from alternative splicing. The domain structure of ST2L includes three extracellular immunoglobulin-like C2 domains, a transmembrane domain, and a cytoplasmic Toll/Interleukin-1 receptor (TIR) domain. sST2 lacks the transmembrane and cytoplasmic domains contained within ST2L and includes a unique 9 amino acid (a.a.) C-terminal sequence (see, e.g., Kakkar et al. Nat. Rev. Drug Disc. 40 7: 827-840, 2008). sST2 can function as a decoy receptor to inhibit soluble IL-33. The term also encompasses naturally occurring variants of ST2, e.g., splice variants (e.g., ST2V, which lacks the third immunoglobulin motif and has a unique hydrophobic tail, and ST2LV, which lacks the transmembrane domain of ST2L) or allelic variants (e.g., variants that are protective against asthma risk or that confer asthma risk as described herein). The amino acid sequence of an exemplary human ST2 can be found, for example, under UniProtKB accession number 001638. ST2 is a part of the IL-33 receptor along with the co-receptor protein IL-1 RAcP. Binding of IL-33 to ST2 and the co-receptor interleukin-1 receptor accessory protein (IL-1 RAcP) forms a 1:1:1 ternary signaling complex to promote downstream signal transduction (Lingel et al. Structure 17(10): 1398-1410, 2009, and Liu et al. Proc. Nat. Acad. Sci. 11 0(37): 14918-14924, 2013).

An "IL-33 axis binding antagonist" refers to a molecule that inhibits the interaction of an IL-33 signaling molecule from binding to one or more of its binding partners. As used herein, an IL-33 axis binding antagonist includes IL-33 antagonists, ST2 antagonists (e.g., ST2L antagonists), and IL-1RAcP antagonists.

As used herein, terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already diagnosed with or suspected of having the disorder. Patients or subjects in need of treatment of treatment can include those diagnosed with coronavirus 2019 (COVID-19) and those who have been infected with severe acute respiratory syndrome coronavirus 2 (SARS-CoV-2).

A "therapeutically effective amount" or "effective amount" refers to an amount of at least one compound of the present disclosure or a pharmaceutical composition comprising at least one such compound that, when administered to a patient, either as a single dose or as part of a series of doses, is effective to produce at least one therapeutic effect. Optimal doses may generally be determined using experimental models and/or clinical trials. The optimal dose of a therapeutic may depend upon the body mass, weight, and/or blood volume of the patient. The level of a compound that is administered to a patient may be monitored by determining the level of the compound (or a metabolite of the compound) in a biological fluid, for example, in the blood, blood fraction (e.g, serum), and/or in the urine, and/or other biological sample from the patient. Any method practiced in the art to detect the compound, or metabolite thereof: may be used to measure the level of the compound during the course of a therapeutic regimen.

As used herein, the terms "subject" and "patient" are used interchangeably. The subject can be an animal. In some aspects, the subject is a mammal such as a non-human animal (e.g., cow, pig, horse, cat, dog, rat, mouse, monkey or other primate, etc.). In some aspects, the subject is a cynomolgus monkey. In some aspects, the subject is a human.

Methods of Treatment

Acute Respiratory Distress Syndrome

The disclosure provides methods for the treatment or prevention of ARDS, or symptoms associated therewith, including hypoxemia and/or excessive pulmonary inflammation. The methods comprise administering to a subject patient an effective amount of an IL-33 axis binding antagonist.

In some instances, the subject is a patient at risk of developing ARDS. As such, the method may be for the prevention of ARDS in a patient at risk thereof.

A subject may be at risk of developing ARDS if they have one or more of the following conditions: pneumonia (viral or bacterial) or severe flu, sepsis, a severe chest injury (e.g. major trauma and/or multiple fractures), aspiration of gastric contents (e.g. accidentally inhaling vomit), smoke or toxic chemicals inhalation, near drowning, pulmonary contusion, fat emboli, pulmonary vasculitis, non-cardiogenic shock or an adverse reaction to a blood transfusion.

These conditions can lead to the development of hypoxemia and or excessive (or "severe") pulmonary inflammation. Therefore, the presence of hypoxemia or excessive pulmonary inflammation in a patient having one or more of the above conditions may be a candidate for treatment with an IL-33 axis binding antagonist to prevent the development of ARDS.

Blocking the IL-33 signaling axis may prevent amplification of the cycle of pulmonary inflammation and cell damage following any of the these conditions or incidents in which the lungs become severely inflamed: pneumonia (viral or bacterial) or severe flu, sepsis, a severe chest injury (e.g. major trauma and/or multiple fractures), aspiration of gastric contents (e.g. accidentally inhaling vomit), smoke or toxic chemicals inhalation, near drowning, pulmonary contusion, fat emboli, pulmonary vasculitis, non-cardiogenic shock or an adverse reaction to a blood transfusion. Severe Pulmonary inflammation caused by these conditions or incidents may cause acute respiratory distress syndrome (ARDS).

Accordingly, the disclosure provides a method of treating or preventing acute respiratory distress syndrome (ARDS), in a patient at risk thereof, comprising administering to the patient an effective amount of an IL-33 axis binding antagonist. In some instances, the method is for the prevention of ARDS in said patient. In some instances, the patient may have excessive pulmonary inflammation.

In some instances, the patient for treatment has mild, moderate, or moderate-to-severe hypoxemia. The presence of hypoxemia indicates that a patient is experiencing sub-optimal gaseous exchange and is at risk of developing ARDS. Therefore, the method may be suitable for a patient who has hypoxemia, in order to reduce or inhibit hypoxemia, thereby preventing the development of ARDS.

In other instances, the disclosure provides a method of treating hypoxemia in a patient, comprising administering to the patient an effective amount of an IL-33 axis binding antagonist. In some instances, the hypoxemia is mild, moderate, or moderate-to-severe hypoxemia.

In some instances, in any of the above methods, the patient may have hypercarbia.

In some instances, the disclosure provides a method of treating excessive pulmonary inflammation in a subject, comprising administering to the patient an effective amount of an IL-33 axis binding antagonist. In some instances, the patient has, or is at risk of developing, ARDS.

In some instances, in any of the above methods, the excessive pulmonary inflammation may be caused by pneumonia (viral or bacterial) or severe flu, sepsis, a severe chest injury (e.g. major trauma and/or multiple fractures), aspiration of gastric contents (e.g. accidentally inhaling vomit), smoke or toxic chemicals inhalation, near drowning, pulmonary contusion, fat emboli, pulmonary vasculitis, non-cardiogenic shock or an adverse reaction to a blood transfusion.

In some instances, the method reduces or inhibits activation of ILC2s. In some instances, the method reduces or inhibits activation of ILC2s in the lungs. In some instances, the method reduces or inhibits IL-5 release from ILC2s.

In some instances, the method reduces or inhibits ccl26 expression in the airway epithelium. In some instances, the method reduces or inhibits ccl26 expression in the lung. CCL26 is chemotactic for eosinophils and basophils. In some instances, therefore, the method reduces chemotaxis of eosinophils or basophils into the lung. It has been found that bronchoalveolar lavage eosinophil counts are low in early-phase ARDS, but increase in late-phase ARDS, while elevated markers of eosinophil activity correlate with ARDS severity. Therefore, reducing or inhibiting ccl26 expression in the lung may reduce chemotaxis of eosinophils to the lung, to thereby prevent or reduce progression of ARDS.

In some instances, in any of the above methods, the patient has pneumonia. In some instances, the pneumonia is viral pneumonia.

In some instances, the patient has coronavirus 2 (SARS-CoV-2) infection. In some instances, in any of the above methods, the ARDS, hypoxemia or excessive pulmonary inflammation is induced by SARS-CoV-2.

In some instances, the patient's arterial oxygen is less than 79 mm HG. In some instances, the patient's partial pressure of oxygen is between 60 and 79 mm HG, inclusive. In some instances, the patient's partial pressure of oxygen is less than 60 mm HG. In some instances, partial pressure of oxygen is between 40 and 59 mmHg, inclusive. In some instances, and severe hypoxemia: the patient's partial pressure of oxygen is 40 mmHg. In some instances, the patient is not or has not yet received mechanical ventilation.

COVID-19

Also disclosed herein is a method of treating or preventing coronavirus disease 2019 (COVID-19) in a patient comprising administering to the patient an effective amount of an IL-33 axis binding antagonist, such as those described herein.

Severe COVID-19 infection is characterized by lung vascular endothelium, airway and alveolar epithelial damage, resulting in cytokine release. This results in alveolar oedema, hypoxemia, acute respiratory distress syndrome (ARDS) and death.

Figure 3:
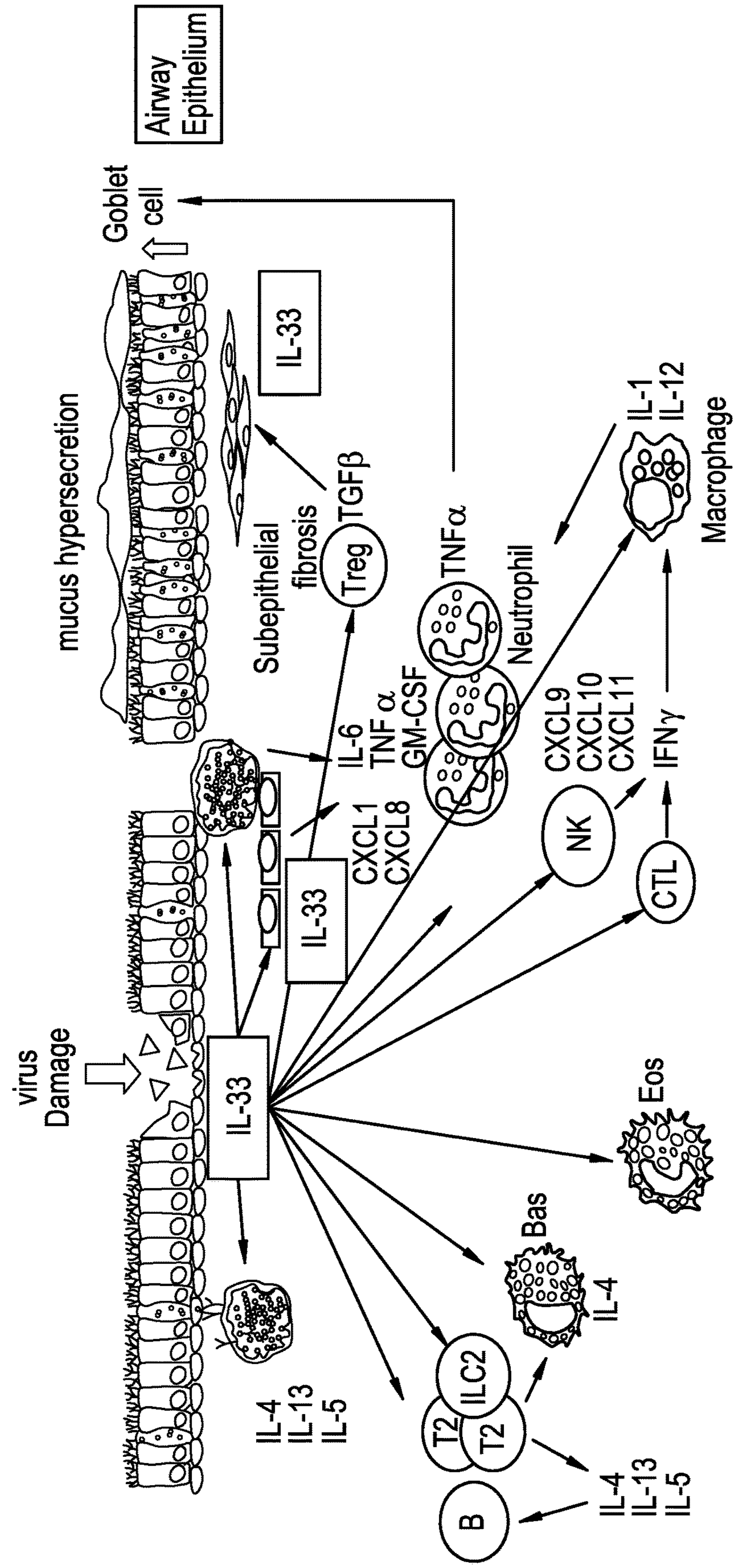
FIG. 3 shows that IL-33 acts as an upstream alarmin cytokine that is rapidly released from lung epithelial and endothelial cells in response to lung injury and cell death.

IL-33 acts as an upstream alarmin cytokine that is rapidly released from lung epithelial and endothelial cells in response to injury and cell death (FIG. 3). This suggests that IL-33 has a pathophysiological role in acute lung injury. The examples show that IL-33 levels are increased in serum of patients at time of hospitalisation following diagnosis with COVID-19 infection.

IL-33 has also been shown to be released in viral driven lung infection, including human rhinovirus, RSV, viral influenza, in response to cell injury and death. Animal models of acute and chronic lung injury are similarly associated with elevated IL-33 and upregulation of T½ cytokines (e.g. IL-6) (Kearley J A et al (2015) *Immunology*). It is also known that COVID-19 is cytopathic, which may result in release of pre-stored IL-33 from pulmonary epithelial and endothelial cells to drive and amplify the cycle of inflammation and cell damage.

As such, IL33 axis binding antagonists may be useful to prevent signaling of IL-33 protein released from the respiratory epithelium and/or endothelium as a consequence COVID-19. Blocking the IL-33 signaling axis may prevent amplification of the cycle of inflammation and cell damage observed in the respiratory tract of COVID-19 patients. In fact blocking the IL-33 signaling axis may prevent amplification of the cycle of pulmonary inflammation and cell damage following any of the these conditions or incidents in which the lungs become severely inflamed: pneumonia (viral or bacterial) or severe flu, sepsis, a severe chest injury (e.g. major trauma and/or multiple fractures), aspiration of gastric contents (e.g. accidentally inhaling vomit), smoke or toxic chemicals inhalation, near drowning, pulmonary contusion, fat emboli, pulmonary vasculitis, non-cardiogenic shock or an adverse reaction to a blood transfusion. Severe Pulmonary inflammation caused by these conditions or incidents may cause acute respiratory distress syndrome (ARDS). Characteristic symptoms of ARDS include severe shortness of breath, rapid shallow breathing, tiredness, drowsiness or confusion, and feeling faint. Suitably therefore, provided herein is a method of treating acute respiratory distress syndrome (ARDS), or one or more symptoms thereof, in a patient, the method comprising administering to the patient an effective amount of an IL-33 axis binding antagonist.

In another aspect, provided herein is a method of treating or preventing coronavirus disease 2019 (COVID-19) in a patient comprising administering to the patient an effective amount of an IL-33 axis binding antagonist. The disclosure also provides for IL-33 axis binding antagonist for use in a method of treating or preventing COVID-19, the method comprising administering an effective amount of an IL-33 axis binding antagonist. The disclosure also provides for the use of an effective amount of an IL-33 axis binding antagonist in a method of treating or preventing COVID-19. The disclosure also provides for the use of an IL-33 axis binding antagonist in the manufacture of a medicament for the treatment of prevention of COVID-19.

In another aspect, provided herein is a method of treating coronavirus disease 2019 (COVID-19) in a patient comprising administering to the patient an effective amount of an IL-33 axis binding antagonist. The disclosure also provides for IL-33 axis binding antagonist for use in a method of treating COVID-19, the method comprising administering an effective amount of an IL-33 axis binding antagonist. The disclosure also provides for the use of an effective amount of an IL-33 axis binding antagonist in a method of treating COVID-19. The disclosure also provides for the use of an IL-33 axis binding antagonist in the manufacture of a medicament for the treatment of prevention of COVID-19.

Suitably, the method may be for preventing or treating acute respiratory insufficiency induced by coronavirus 2 (SARS-CoV-2) infection in a patient comprising administering to the patient an effective amount of an IL-33 axis binding antagonist. The disclosure also provides for IL-33 axis binding antagonist for use in a method of treating or preventing acute respiratory insufficiency induced by coronavirus 2 (SARS-CoV-2), the method comprising administering an effective amount of an IL-33 axis binding antagonist. The disclosure also provides for the use of an effective amount of an IL-33 axis binding antagonist in a method of treating or preventing acute respiratory insufficiency induced by severe acute respiratory syndrome coronavirus 2 (SARS-CoV-2). The disclosure also provides for the use of an IL-33 axis binding antagonist in the manufacture of a medicament for the treatment of prevention of acute respiratory insufficiency induced by coronavirus 2 (SARS-CoV-2). Suitably, the methods, compositions or uses may be for preventing or treating worsening acute respiratory insufficiency induced by coronavirus 2 (SARS-CoV-2) infection in a patient comprising administering to the patient an effective amount of an IL-33 axis binding antagonist.

Suitably, the method may be for preventing or treating acute respiratory distress syndrome (ARDS) induced by coronavirus 2 (SARS-CoV-2) infection in a patient comprising administering to the patient an effective amount of an IL-33 axis binding antagonist. The disclosure also provides for IL-33 axis binding antagonist for use in a method of treating or preventing ARDS induced by coronavirus 2 (SARS-CoV-2), the method comprising administering an effective amount of an IL-33 axis binding antagonist. The disclosure also provides for the use of an effective amount of an IL-33 axis binding antagonist in a method of treating or preventing ARDS induced by severe acute respiratory syndrome coronavirus 2 (SARS-CoV-2). The disclosure also provides for the use of an IL-33 axis binding antagonist in the manufacture of a medicament for the treatment of prevention of acute respiratory insufficiency induced by coronavirus 2 (SARS-CoV-2).

Suitably, the method of treating and/or preventing excessive pulmonary inflammation in a patient infected by SARS-CoV-2 or a patient with COVID-19 comprising administering to the patient an effective amount of an IL-33 axis binding antagonist. The disclosure also provides for IL-33 axis binding antagonist for use in a method of treating or preventing excessive pulmonary inflammation in a patient infected by SARS-CoV-2 or a patient with COVID-19, the method comprising administering an effective amount of an IL-33 axis binding antagonist. The disclosure also provides for the use of an effective amount of an IL-33 axis binding antagonist in a method of treating or preventing excessive pulmonary inflammation in a patient infected by SARS-CoV-2 or a patient with COVID-19. The disclosure also provides for the use of an IL-33 axis binding antagonist in the manufacture of a medicament for the treatment of prevention of cytokine storm in a patient infected by SARS-CoV-2 or a patient with COVID-19. An example of excessive pulmonary inflammation is "cytokine storm syndrome" (CSS) or "cytokine release syndrome" (CRS). CSS is a form of systemic inflammatory response syndrome that can occur when large numbers of white blood cells are activated and release inflammatory cytokines, which in turn activate yet more white blood cells. As shown in FIG. 3 damage to the lung epithelium and/or alveolar endothelium induced by COVID-19 may lead to a release of IL-33. Release of IL33 induces a cascade of inflammatory responses than can lead to the recruitment and activation of a large number of white blood cells (innate lymphoid Type 2 cells (ILC2), eosinophils, natural killer cells, etc). Recruitment and activation of a large number of white blood cells may drive and amplify the cycle of inflammation leading to CSS or CRS. Predictors of fatality from a recent retrospective, multicentre study of 150 confirmed COVID-19 cases in Wuhan, China, included elevated ferritin and IL-6, suggesting that mortality might be due to virally driven hyperinflammation (Ruan Q et al (2020) *Intensive Care Med*). Given therefore that IL-33 is a master regulator of inflammation in response to lung epithelium damage, inhibition of IL-33 may be effective in the treatment or prevention of excessive pulmonary inflammation in a patient, for example in a patient infected by SARS-CoV-2.

In some instances of the methods, compounds for use, and uses provided herein, the patient has confirmed or suspected COVID-19 requiring hospitalization. In some instances of the methods, compounds for use, and uses provided herein, the patient has confirmed COVID-19 requiring hospitalization. In some instances of the methods, compounds for use, and uses provided herein, the patient has SARS-CoV-2 infection confirmed by laboratory tests and/or point of care tests. In some instances of the methods, compounds for use, and uses provided herein, the patient is an adult (≥18 years).

In some instances of the methods, compounds for use, and uses provided herein, the patient to be treated has a score of Grade 3 to 5 on the WHO's 9 Point Category Ordinal Scale.

WHO's 9 Point Category Ordinal Scale for Clinical Improvement:

0. Uninfected, no clinical or biological evidence of infection
1. Not hospitalised, no limitations on activities
2. Not hospitalised, limitation on activities
3. Hospitalised, not requiring supplemental oxygen
4. Hospitalised, requiring supplemental oxygen
5. Hospitalised, on non-invasive ventilation or high flow oxygen devices
6. Hospitalised, intubation and mechanical ventilation
7. Hospitalised, ventilation and additional organ support (ECMO)
8. Death In some instances of the methods, compounds for use, and uses provided herein, the patient has hypoxemia.

In some instances of the methods, compounds for use, and uses provided herein, the patient has one or more of the following conditions: a lung condition, such as asthma, COPD, emphysema or bronchitis; heart disease, such as heart failure; chronic kidney disease; liver disease, such as hepatitis; conditions affecting the brain and nerves, such as Parkinson's disease, motor neuron disease, multiple sclerosis (MS or cerebral palsy; diabetes, such as Type 1 or Type 2 diabetes; sickle cell disease or if the patient has had their spleen removed; and/or a compromised immune system, such as wherein the patient has HIV or AIDS, or wherein the patient is undergoing chemotherapy.

In some instances of the methods, compounds for use, and uses provided herein, the patient in clinically obese. In some instances, the patient has a BMI of 40 or above.

In some instances of the methods, compounds for use, and uses provided herein, the patient has pneumonia. The pneumonia can be pneumonia that has been confirmed by chest imaging. In some instances, the pneumonia is viral pneumonia. In some instances, the pneumonia is induced by SARS-CoV-2 infection. In some instances, the pneumonia is induced by influenza virus A, influenza virus B, respiratory syncytial virus, human parainfluenza virus, adenovirus, metapneumovirus, SARS-COV, Middle East respiratory syndrome virus (MERS-CoV), hantavirus, herpes simplex virus, varicella-zoster virus, measles virus, rubella virus, cytomegalovirus, smallpox virus or dengue virus. In some instances, the pneumonia is induced by influenza virus A, influenza virus B, respiratory syncytial virus or human parainfluenza virus.

In some instances, the methods, compounds for use, and uses provided herein significantly reduce the need for the patient to receive respiratory support, for example, invasive or non-invasive respiratory support, such as mechanical ventilation or Extracorporeal membrane oxygenation (ECMO).

In some of the methods, compounds for use, and uses provided herein, the patient is human. In some instances, the patient is at least 40 years of age, at least 50 years of age, at least 60 years of age, at least 70 years of age, at least 80 years old, or at least 90 years old.

In some instances, the methods, compounds for use, and uses provided herein, extend to length of time to death and/or improve the rate of survival.

In some instances, the methods, compounds for use, and uses provided herein, lead to a clinical improvement of at least 2 points on the 9-point category ordinal scale by Day 29 or earlier (wherein Day 1 is defined as the day on which the patient is administered a first dose of the therapy defined herein).

In some instances, the methods, compounds for use, and uses provided herein, reduce the time to discharge from hospital.

In some instances, the methods, compounds for use, and uses provided herein, reduce the time to the subject being considered fit for discharge (a score of 0, 1, or 2 on the 9-point category ordinal scale).

In some instances, the methods, compounds for use, and uses provided herein, reduce the deterioration of the subject according to the ordinal scale by 1, 2, or 3 points on Days 2, 8, 15, 22, and 29 (wherein Day 1 is defined as the day on which the patient is administered a first dose of the therapy defined herein).

Exemplary embodiments of methods of treating COVID-19, or associated features of the disease, include:

1. A method of treating or preventing coronavirus disease 2019 (COVID-19) in a patient, the method comprising administering to the patient an effective amount of an anti-IL33 antibody, or antigen binding fragment thereof, comprising a VHCDR1 having the sequence of SEQ ID NO: 37, a VHCDR2 having the sequence of SEQ ID NO: 38, a VHCDR3 having the sequence of SEQ ID NO: 39, a VLCDR1 having the sequence of SEQ ID NO: 40, a VLCDR2 having the sequence of SEQ ID NO: 41, and a VLCDR3 having the sequence of SEQ ID NO: 42.
2. A method of preventing or treating acute respiratory insufficiency induced by coronavirus 2 (SARS-CoV-2) infection in a patient, the method comprising administering to the patient an effective amount of the anti-IL33 antibody, or antigen binding fragment thereof, defined in embodiment 1.
3. A method of preventing or treating acute respiratory distress syndrome (ARDS) induced by coronavirus 2 (SARS-CoV-2) infection in a patient, the method comprising administering to the patient an effective amount of the anti-IL33 antibody, or antigen binding fragment thereof, defined in embodiment 1.
4. A method of treating or preventing excessive pulmonary inflammation in a patient infected by SARS-CoV-2 or a patient with COVID-19, the method comprising administering to the patient an effective amount of the anti-IL33 antibody, or antigen binding fragment thereof, defined in embodiment 1.
5. The method of any preceding embodiment, wherein the patient has confirmed or suspected COVID-19 requiring hospitalization.
6. The method of any preceding embodiment, wherein the patient has respiratory distress and/or hypoxemia.
7. The method of any preceding embodiment, wherein the patient has one or more of the following conditions:
    a. a lung condition, such as asthma, COPD, emphysema or bronchitis;
    b. heart disease, such as heart failure;
    c. chronic kidney disease;
    d. liver disease, such as hepatitis;
    e. a condition affecting the brain and nerves, such as Parkinson's disease, motor neuron disease, multiple sclerosis (MS or cerebral palsy;
    f. diabetes, such as Type 1 or Type 2 diabetes;
    g. sickle cell disease or if the patient has had their spleen removed; and/or
    h. a compromised immune system, such as wherein the patient has HIV or AIDS, or wherein the patient is undergoing chemotherapy.
8. The method of any preceding embodiment, wherein the patient has a BMI of 40 or above.
9. The method of any preceding embodiment, wherein the patient has pneumonia.
10. The method of any preceding embodiment, wherein the treatment significantly reduces the need for the patient to receive respiratory support.
11. The method of embodiment 10, wherein the respiratory support is invasive or non-invasive.
12. The method of any preceding claim, wherein the patient is at least 40 years of age, at least 50 years of age, at least 60 years of age, at least 70 years of age, at least 80 years old, or at least 90 years old
13. The method of any preceding embodiment, wherein the antibody, or antigen binding fragment thereof is to be administered to the patient parenterally, for example intravenously or subcutaneously.
14. The method of any preceding embodiment, wherein the VH and VL of said antibody or antigen-binding fragment thereof comprise amino acid sequences at least 95%, 90%, or 85% identical to SEQ ID NO: 1 and SEQ ID NO: 19, respectively.
15. The method of embodiment 14, wherein the antibody or antigen binding fragment thereof, comprises a VH having the sequence of SEQ ID NO: 1 and a VL having the sequence of SEQ ID NO: 19.
16. The method of any preceding embodiment, wherein the antibody or antigen binding fragment thereof is selected from a human antibody, a chimeric antibody, and a humanized antibody.
17. The method of any preceding embodiment, wherein the antibody or antigen binding fragment thereof is selected from a naturally-occurring antibody, an scFv fragment, an Fab fragment, an F(ab')2 fragment, a minibody, a diabody, a triabody, a tetrabody, and a single chain antibody.
18. The method of any preceding embodiment, wherein the antibody or antigen binding fragment thereof is a monoclonal antibody.
19. The method of any preceding embodiment, wherein the antibody is administered to the patient in a pharmaceutically acceptable form.

IL-33 Levels as a Biomarker for Treatment

In some instances, the method is for a patient with increased levels of total serum IL-33, compared to baseline levels. The examples show IL-33 levels are elevated in subjects with COVID-19. Hospitalized subjects with COVID-19 can go on to develop symptoms of ARDS. Therefore, identifying subjects with elevated levels of IL-33 and who are presenting symptoms associated with the development of ARDS (e.g., hypoxemia or severe pulmonary inflammation), may enable the early identification of patients at increased of developing ARDS associated with increased IL-33 activity.

The examples also show that human rhinovirus infection drives activation of ILC2s in an IL-33-dependent manner. ILC2 hyper-activation has been linked to onset of ARDS. Therefore, it is plausible that increased IL-33 activity may be a common pathological mechanism within pneumonias (such as viral pneumonias) that leads to the development of ARDS.

Accordingly, the methods disclosed herein may be for patients who have high levels of IL-33. In some instances, the patient may have high levels of serum IL-33. In some instances, the patient may have high levels of serum IL-33/sST2 complex.

The level of IL-33, either alone or in complex with sST2, may be determined by any one of a number of assay available in the art.

For example, the level of IL-33 (or IL-33/sST2 complex) may be determined by immunoassay.

Immunoassays typically require capture reagents, such as antibodies, to capture the relevant analyte, and optionally probe reagents, to detect the relevant analyte. Suitable immunoassay techniques are: ELISA (enzyme linked immunosorbent assay), S-plex, western blotting, immunocytochemistry, immunoprecipitation, affinity chromotography, Bio-Layer Interferometry, Octet, ForteBio) and biochemical assays such as Dissociation-Enhanced Lanthanide Fluorescent Immunoassays (DELFIA®, Perkin Elmer), Forster resonance energy transfer (FRET) assays (e.g. homogeneous time resolved fluorescence (HTRF®, Cis Biointernational), and radioimmuno/radioligand binding assays.

Western blot analysis generally comprises preparing protein samples, electrophoresis of the protein samples in a polyacrylamide gel (e.g., 8-20 SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 1251) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding Western blot protocols see, e.g., Ausubel et al., eds, (1994) Current Protocols in Molecular Biology (John Wiley & Sons, Inc., NY) Vol. 1 at 10.8.1.

ELISAs comprise preparing antigen, coating the well of a 96-well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, (1994) Current Protocols in Molecular Biology (John Wiley & Sons, Inc., NY) Vol. 1 at 13.2.1.

In some instances, the level of IL-33 may be determined by using a modified ELISA called an S-plex assay. S-plex assays are available from Meso Scale Diagnostics LLC with suitable instructions for use.

"High level" as used herein means a level higher than a baseline value. A baseline value for IL-33 may be a predetermined amount of IL-33 or IL-33/sST2 determined from a cohort of healthy control subjects, or it could mean a baseline level of IL-33 or IL-33/sST2 previously measured in the patient. For example, such a measurement may have been determined earlier during care for the subject, for example, a measurement obtained before the patient was admitted to hospital with a pre-condition increasing susceptibility to ARDS (e.g., if patient has pneumonia).

In some instances, therefore, the methods disclosed herein are for patients with IL-33 levels greater than a control value, serum IL-33 levels greater than a control value or serum IL-33/sST2 complex levels greater than a control value.

In some instances, the control value comprises a predefined vale of IL-33 obtained from healthy control subjects. In some instances, the control value comprises a previous value of IL-33 levels obtained from the patient.

This biomarker analysis may enable identification of patients who have received a lung insult (e.g., viral infection, trauma, etc.) and are therefore at risk of developing ARDS. Such a scenario enables prevention of ARDS by early intervention prior to manifestation of ARDS or symptoms associated therewith.

As such, the methods disclosed herein may be for the prevention of ARDS, particularly where in a patient is at risk of developing ARDS, for example, since they are known or have received an insult to the lungs.

In some instances, the method comprises the step of measuring the patient's IL-33 levels, and, wherein the patient has IL-33 levels that exceed the control IL-33 value, selecting them for treatment with the methods disclosed herein.

In some instances, the method is for use in a patient, wherein the patient has been determined to comprise IL-33 levels that exceed the control IL-33 value.

IL-33 Axis Binding Antagonists

In some instances, the methods, compounds for use, and uses provided herein, reduce the use of clinically administered oxygen.IL-33 Axis Binding Antagonists.

IL-33 axis binding antagonists that may be suitable for use in the methods disclosed herein include anti-IL-33 antibodies or antigen binding fragments thereof, including 33_640087-7B (as described in WO2016/156440), ANB020 known as etokimab (as described in WO2015/106080), 9675P (as described in US2014/0271658), A25-3H04 (as described in US2017/0283494), Ab43 (as described in WO2018/081075), IL33-158 (as described in US2018/0037644), 10C12.38.H6. 87Y.581 lgG4 (as described in WO2016/077381) or binding fragments thereof. Other exemplary anti-IL-33 antibodies or antigen binding fragments thereof include any of the other anti-IL-33 antibodies described in WO2016/156440, WO2015/106080, US2014/0271658, US2017/0283494, WO2018/081075, US2018/0037644 or WO2016/077381, all of which are incorporated herein by reference.

Other exemplary IL-33 axis binding antagonists include polypeptides that bind IL-33 and/or its receptor (ST-2) or co-receptor (IL1-RAcP) and block ligand receptor interaction (e.g., ST2-Fc proteins, such as those described in WO2013/173761; WO2013/165894; or WO2014/152195, each of which are incorporated herein by reference in their entirety, or soluble ST2, or derivatives thereof).

Other exemplary IL-33 axis binding antagonists also include anti-ST-2 antibodies or antigen binding fragments thereof (e.g., AMG-282 (Amgen) or STLM15 (Janssen) or any of the anti-ST2 antibodies described in WO2013/173761 or WO2013/165894, which are each incorporated herein by reference in their entirety).

Other exemplary IL-33 axis binding antagonists include IL-33 receptor-based ligand trap, such as those described in WO2018/102597, which is incorporated herein by reference.

In one instance the IL-33 axis binding antagonist is a binding molecule. Suitably, the binding molecule may be an antibody or antigen-binding fragment thereof.

Suitably, the binding molecule specifically binds to IL-33. Such a binding molecule is also referred to as an "IL-33 binding molecule" or an "anti-IL-33 binding molecule". Suitably, the binding molecule specifically binds to IL-33 and inhibits or attenuates IL-33 activity.

Suitably the IL-33 binding molecule binds specifically to reduced IL-33, oxidised IL-33 or both reduced IL-33 and oxidised IL-33.

Suitably, the binding molecule may attenuate or inhibit IL-33 activity by binding IL-33 in reduced or oxidised forms. Suitably, wherein the binding molecule inhibits or attenuates reduced IL-33 activity and oxidised IL-33 activity, this is achieved by binding to IL-33 in reduced form (i.e. by binding to reduced IL-33).

Suitably, the binding molecule inhibits or attenuates the activity of both redIL-33 and oxIL-33, thereby inhibiting or attenuating both ST2 signaling and oxIL-33 activity. Recently ox-IL33, but not red-IL-33, binds to the receptor for advanced glycation end products (RAGE). Ox-IL33-dependent RAGE signaling has been shown to inhibit epithelial cell proliferation and migration.

Suitably, the binding molecule may specifically bind to redIL-33 with a binding affinity (Kd) of less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-2}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M. Suitably, the binding affinity to redIL-33 is less than $5\times10^{-14}$ M (i.e. 0.05 pM). Suitably, the binding affinity is as measured using Kinetic Exclusion Assays (KinExA) or BIACORE™, suitably using KinExA, using protocols such as those described in WO2016/156440 (see e.g., Example 11), which is hereby incorporated by reference in its entirety. It has been found that binding molecules that bind to redIL-33 with this binding affinity bind tightly enough to prevent dissociation of the binding molecule/redIL-33 complex within biologically relevant timescales. Without wishing to be bound by theory, this binding strength is thought to prevent release of the antigen prior to degradation of the binding molecule/antigen complex in vivo, minimizing any IL-33-dependent activity associated with IL-33 release from the binding complex.

Suitably, the binding molecule may specifically bind to redIL-33 with an on rate (k(on)) of greater than or equal to $10^3$ $M^{-1}$ $sec^{-1}$, $5\times10^3$ $M^{-1}$ $sec^{-1}$, $10^4$ $M^{-1}$ $sec^{-1}$ or $5\times10^4$ $M^{-1}$ $sec^{-1}$. For example, a binding molecule of the disclosure may bind to redIL-33 or a fragment or variant thereof with an on rate (k(on)) greater than or equal to $10^5$ $M^{-1}$ $sec^{-1}$, $5\times10^5$ $M^{-1}$ $sec^{-1}$, $10^6$ $M^{-1}$ $sec^{-1}$, or $5\times10^6$ $M^{-1}$ $sec^{-1}$ or $10^7$ $M^{-1}$ $sec^{-1}$. Suitably, the k(on) rate is greater than or equal to $10^7$ $M^{-1}$ $sec^{-1}$. Suitably, the binding molecule may specifically bind to redIL-33 with an off rate (k(off)) of less than or equal to $5\times10^{-1}$ $sec^{-1}$, $10^{-1}$ $sec^{-1}$, $5\times10^{-2}$ $sec^{-1}$, $10^{-2}$ $sec^{-1}$, $5\times10^{-3}$ $sec^{-1}$ or $10^{-3}$ $sec^{-1}$. For example, a binding molecule of the disclosure may be said to bind to redIL-33 or a fragment or variant thereof with an off rate (k(off)) less than or equal to $5\times10^{-4}$ $sec^{-1}$, $10^{-4}$ $sec^{-1}$, $5\times10^{-5}$ $sec^{-1}$, or $10^{-5}$ $sec^{-1}$, $5\times10^{-6}$ $sec^{-1}$, $10^{-6}$ $sec^{-1}$, $5\times10^{-7}$ $sec^{-1}$ or $10^{-7}$ $sec^{-1}$. Suitably, the k(off) rate is less than or equal to $10^{-3}$ $sec^{-1}$. IL-33 is an alarmin cytokine released rapidly and in high concentrations in response to inflammatory stimuli. redIL-33 is converted to the oxidised approximately 5-45 mins after release into the extracellular environment (Cohen et al Nat Commun 6, 8327 (2015)). Without wishing to be bound by theory, binding to redIL-33 with these k(on) and/or k(off) rates may minimize exposure to redIL-33 prior to conversion of the reduced from to oxIL-33. Moreover, the k(off) rate may prevent IL-33 release from the binding molecule/antigen complex prior to degradation of the complex in vivo. These binding kinetics may also act to prevent conversion of redIL-33 to oxIL-33, and thus prevent pathological signaling of the oxidised form of IL-33 via RAGE (described in WO2016/156440, which is incorporated herein by reference).

Suitably, the IL-33 binding molecule may competitively inhibit binding of IL-33 to any of the binding molecules referenced in Table 1:

TABLE 1

Exemplary anti-IL-33 antibody VH and VL pairs

| Pair | SEQ ID NO: | HCVR amino acid sequence | NO: | LCVR amino acid sequence |
|---|---|---|---|---|
| 1 | SEQ ID NO: 1 | EVQLLESGGGLVQPGGS LRLSCAASGFTFSSYAM SWVRQAPGKGLEWVSG ISAIDQSTYYADSVKGR FTISRDNSKNTLYLQMN SLRAEDTAVYYCARQK FMQLWGGGLRYPFGY WGQGTMVTVSS | SEQ ID NO: 19 | SYVLTQPPSVSVSPGQ TASITCSGEGMGDKYA AWYQQKPGQSPVLVI YRDTKRPSGIPERFSGS NSGNTATLTISGTQAM DEADYYCGVIQDNTG VFGGGTKLTVL |
| 2 | SEQ ID NO: 2 | EVQLVESGGGLVQPGGS LRLSCAASGFTFRSFAM SWVRQAPGKGLELVSD LRTSGGSTYYADSVKGR LTISRDNSKNTLYLQMN SLRAEDTAVYYCAKSH YSTSWFGGFDYWGQGT LVTVSS | SEQ ID NO: 20 | DIQMTQSPSSVSASVG DRVTITCRASQGFSSW LAWYQQKPGKAPKLLI YAASSLQSGVPSRFSG SGSGTDFTLTITNLQPE DFATYYCQQANSFPLT FGGGTKVEIK |
| 3 | SEQ ID NO: 3 | QVQLQESGPGLVKPSET LSLTCTVSGGSISSYYWS WIRQPPGKGLELIGYIYY SGSTNYNPSLKSRVTISV DTSKNHFSLKLSSVTAA DTAVYYCARSQYTSSW YGSFDIWGQGTMVTVS S | SEQ ID NO: 21 | DIQMTQSPSSVSASVG DRVTITCRASQGISTW LAWFQQKPGKAPKLLI YAASTLQGGVPSRFSG SGSGPEFTLTISSLQPE DFATYYCQQANSFPW TFGQGTKVEIK |

TABLE 1-continued

Exemplary anti-IL-33 antibody VH and VL pairs

| Pair | SEQ ID NO: | HCVR amino acid sequence | NO: | LCVR amino acid sequence |
|---|---|---|---|---|
| 4 | SEQ ID NO: 4 | QVQLVQSGAEVKKPGASVKVSCKASGYTFNSYGISWVRQAPGQGLEWMGWISSHNGNSHYVQKFQGRVSMTTDTSTSTAYMELRSLRSDDTAVYYCARHSYTTSWYGGFDYWGQGTLVTVSS | SEQ ID NO: 22 | DIQMTQSPSSVSASVGDRVTITCRASQGFSSWLAWYQQKPGKAPQLLIYAASSLQSGVPSRFSGSGSGSDFTLTISSLQPEDFATYYCQQANSFPLTFGGGTKVEIK |
| 5 | SEQ ID NO: 5 | EVQLVESGGGLVQPGGSLRLSCAASGFTFSSYALTWVRQAPGKGLEWVSFISGSGGRPFYADSVKGRFTISRDNSKNMLYLQMNSLRAEDTAIYYCAKSLYTTSWYGGFDSWGQGTLVTVSS | SEQ ID NO: 23 | DIQMTQSPSSVSASVGDRVTITCRASQGVVSWLAWYQQKPGKAPKLLIYAASSLQSGVPSRFSGSGSGTDFTLTISSLQPEDFATYYCQQSNSFPFTLGPGTKVDIK |
| 6 | SEQ ID NO: 6 | EVQLVESGGGLVQPGGSLRLSCAASGFTFSNYAMTWVRQAPGKGLEWVSTISGSGDNTYYADSVQGRFTISRGHSKNTLYLQMNSLRAEDTAVYYCAKPTYSRSWYGAFDFWGQGTMVTVSS | SEQ ID NO: 24 | DIQMTQSPSSVSASVGDRVTITCRASQGISSWLAWYQQKPGKAPQLLIYAASRLQSGVPSRFWGSGSGTDFTLTISSLQPEDFATYYCQQANNFPFTFGPGTKVDIK |
| 7 | SEQ ID NO: 7 | EVQLVESGGNLEQPGGSLRLSCTASGFTFSRSAMNWVRRAPGKGLEWVSGISGSGGRTYYADSVKGRFTISRDNSKNTLYLQMNSLSAEDTAAYYCAKDSYTTSWYGGMDVWGHGTTVTVSS | SEQ ID NO: 25 | DIQMTQSPSSVSASVGDRVTITCRASQGIFSWLAWYQQKPGKAPKLLIYAASSLQSGVPSRFSGSGSGTDFTLTISSLQPEDFAIYYCQQANSVPITFGQGTRLEIK |
| 8 | SEQ ID NO: 8 | EVQLLESGGGLVQPGGSLRLSCAASGFTFSDYYMNWVRQAPGKGLEWVSSISRYSSYIYYADSVKGRFTISRDNSKNTLYLQMNSLRAEDTAVYYCARDIGGMDVWGQGTLVTVSS | SEQ ID NO: 26 | QSVLTQPPSASGTPGQRVTISCTGSSSNIGAVYDVHWYQQLPGTAPKLLIYRNNQRPSGVPDRFSGSKSGTSASLAISGLRSEDEADYYCQTYDSSRWVFGGGTKLTVL |
| 9 | SEQ ID NO: 9 | EVQLLESGGGLVQPGGSLRLSCAASGFTFSNYYMHWVRQAPGKGLEWVSSISARSRYHYYADSVKGRFTISRDNSKNTLYLQMNSLRAEDTAVYYCARLATRHNAFDIWGQGTLVTVSS | SEQ ID NO: 27 | QSVLTQPPSASGTPGQRVTISCSGSSSNIGNNAVSWYQQLPGTAPKLLIYASNMRVIGVPDRFSGSKSGTSASLAISGLRSEDEADYYCGAWDDSQKALVFGGGTKLTVL |
| 10 | SEQ ID NO: 10 | EVQLLESGGGLVQPGGSLRLSCAASGFTFSNYYMHWVRQAPGKGLEWVSSISARSSYIYYADSVKGRFTISRDNSKNTLYLQMNSLRAEDTAVYYCARLATRNNAFDIWGQGTLVTVSS | SEQ ID NO: 28 | QSVLTQPPSASGTPGQRVTISCSGSSSNIGRNAVNWYQQLPGTAPKLLIYASNMRVSGVPDRFSGSKSGTSASLAISGLRSEDEADYYCWAWDDSQKVGVFGGGTKLTVL |
| 11 | SEQ ID NO: 11 | EVQLLESGGGLVQPGGSLRLSCAASGFTFSRYYMHWVRQAPGKGLEWVSSISAQSSHIYYADSVEGRFTISRDNSKNTLYLQMNSLRAEDTAVYYCARLATRQNAFDIWGQGTLVTVSS | SEQ ID NO: 29 | QSVLTQPPSASGTPGQRVTISCSGSSSNIGRNAVNWYQQLPGTAPKLLIYASNMRRSGVPDRFSGSKSGTSASLAISGLRSEDEADYYCSAWDDSQKVVVFGGGTKLTVL |
| 12 | SEQ ID NO: 12 | EVQLLESGGGLVQPGGSLRLSCAASGFTFSNYYMHWVRQAPGKGLEWVSS | SEQ ID NO: 30 | QSVLTQPPSASGTPGQRVTISCSGSSSNIGNNAVNWYQQLPGTAPKLLI |

TABLE 1-continued

| Exemplary anti-IL-33 antibody VH and VL pairs | | | | |
|---|---|---|---|---|
| Pair | SEQ ID NO: | HCVR amino acid sequence | NO: | LCVR amino acid sequence |
| | | ISARSSYLYYADSVKGR FTISRDNSKNTLYLQMN SLRAEDTAVYYCARLA TRHVAFDIWGQGTLVT VSS | | YASNMRRPGVPDRFSG SKSGTSASLAISGLRSE DEADYYCEAWDDSQK AVVFGGGTKLTVL |
| 13 | SEQ ID NO: 13 | MRAWIFFLLCLAGRALA QVQLMQSGAEVKKPGA SVKVSCKASGYTFTSY WMHWVRQAPGQGLEW MGTIYPRNSNTDYNQKF KARVTMTRDTSTSTVY MELSSLRSEDTAVYYCA RPLYYYLTSPPTLFWGQ GTLVTVSS | SEQ ID NO: 31 | MRAWIFFLLCLAGRAL ADIQLTQSPSFLSASVG DRVTITCKASQDVGTA VAWYQQKPGKAPKLL IYWASTRHTGVPSRFS GSGSGTEFTLTISSLQP EDFATYYCQQAKTYPF TFGSGTKLEIKR |
| 14 | SEQ ID NO: 14 | EVQLVETGGGLIQPGGS LRLSCAASGFTFSSYAM SWVRQAPGKGLEWVSA ISGSGGSTYYADSVKGR FTISRDNSKNTLYLQMN SLRAEDTAVYYCARTL HGIRAAYDAFIIWGQGT LVTVSS | SEQ ID NO: 32 | EIVLTQSPGTLSLSPGE RATLSCRASQSVGINLS WYQQKPGQAPRLLIY GASHRATGIPDRFSGS GSGTDFTLTISRLEPED FAVYYCHQYSQSPPFT FGGGTKVEIK |
| 15 | SEQ ID NO: 15 | EVQLVETGGGLIQPGGS LRLSCAASGFTFSFYAM SWVRQAPGKGLEWVSA ISGSGGSTYYADSVKGR FTISRDNSKNTLYLQMN SLRAEDTAVYYCARTL HGIRAAYDAFIIWGQGT LVTVSS | SEQ ID NO: 33 | EIVLTQSPGTLSLSPGE RATLSCRASQSVGINLS WYQQKPGQAPRLLIY GASHRLTGIPDRFSGSG SGTDFTLTISRLEPEDF AVYYCHQYSQPPPFTF GGGTKVEIK |
| 16 | SEQ ID NO: 16 | EVQLVETGGGLIQPGGS LRLSCAASGFTFSFYAM SWVRQAPGKGLEWVSA ISGSGGSTYYADSVKGR FTISRDNSKNTLYLQMN SLRAEDTAVYYCARTIH GIRAAYDAFIIWGQGTL VTVSS | SEQ ID NO: 34 | EIVLTQSPGTLSLSPGE RATLSCRASQSVGINLS WYQQKPGQAPRLLIY GASHRLTGIPDRFSGSG SGTDFTLTISRLEPEDF AVYYCHQYSQPPPFTF GGGTKVEIK |
| 17 | SEQ ID NO: 17 | EVQLVESGGGLVQPGGS LRLSCAASGFTFSSYWM YWVRQAPGKGLEWVA AITPNAGEDYYPESVKG RFTISRDNAKNSLYLQM NSLRAEDTAVYYCARG HYYYTSYSLGYWGQGT LVTVSS | SEQ ID NO: 35 | DIQMTQSPSSLSASVG DRVTITCKASQNINKH LDWYQQKPGKAPKLLI YFTNNLQTGVPSRFSG SGSGTDFTLTISSLQPE DFATYYCFQYNQGWT FGGGTKVEIK |
| 18 | SEQ ID NO: 18′ | EVQLVESGGGLVQPGGS LRLSCAASGFTFSSFSMS WVRQAPGKGLEWVATI SGGKTFTDYVDSVKGRF TISRDDSKNTLYLQMNS LRAEDTAVYYCTRANY GNWFFEVWGQGTLVTV SS | SEQ ID NO: 36 | EIVLTQSPATLSLSPGE RATLSCRASESVAKYG LSLLNWFQQKPGQPPR LLIFAASNRGSGIPARF SGSGSGTDFTLTISSLE PEDFAVYYCQQSKEVP FTFGQGTKVEIK |

All these binding molecules have been reported to bind to IL-33 and inhibit or attenuate ST-2 signaling. Thus, a binding molecule or binding fragment thereof that competes for binding to IL-33 with any of the antibodies described in Table 1 may inhibit or attenuate ST-2 signaling.

A binding molecule or fragment thereof is said to competitively inhibit binding of a reference antibody to a given epitope if it specifically binds to that epitope to the extent that it blocks, to some degree, binding of the reference antibody to the epitope. Competitive inhibition may be determined by any method known in the art, for example, solid phase assays such as competition ELISA assays, Dissociation-Enhanced Lanthanide Fluorescent Immunoassays (DELFIA®, Perkin Elmer), and radioligand binding assays. For example, the skilled person could determine whether a binding molecule or fragment thereof competes for binding to IL-33 by using an in vitro competitive binding assay, such as the HTRF assay described in WO2016/156440, paragraphs 881-886, which is incorporated herein by reference. For example, the skilled person could label a recombinant antibody of Table 6 with a donor fluorophore and mix multiple concentrations with fixed concentration samples of acceptor fluorophore labelled-redIL-33. Subsequently, the fluorescence resonance energy transfer between the donor and acceptor fluorophore within each sample can be measured to ascertain binding characteristics. To elucidate competitive binding molecules the skilled person could first mix various concentrations of a test binding molecule with a fixed concentration of the labelled antibody of Table 6. A reduction in the FRET signal when the mixture is incubated with labelled IL-33 in comparison with a labelled antibody-only positive control would indicate competitive binding to IL-33. A binding molecule or fragment thereof may be said to competitively inhibit binding of the reference antibody to a given epitope by at least 90%, at least 80%, at least 70%, at least 60%, or at least 50%.

Suitably, the IL-33 binding molecule may be an antibody or antigen-binding fragment comprising the complementarity determining regions (CDRs) of a variable heavy domain (VH) and a variable light domain (VL) pair selected from Table 1. Therein, pair 1 corresponds to the VH and VL domain sequences of 33_640087-7B described in WO2016/156440. Pairs 2-7 correspond to VH and VL domain sequences of antibodies described in US2014/0271658. Pairs 8-12 correspond to VH and VL domain sequences of antibodies described in US2017/0283494. Pair 13 corresponds to the VH and VL domain sequences of ANB020, described in WO2015/106080. Pairs 14-16 correspond to VH and VL domain sequences of antibodies described in WO2018/081075. Pair 17 corresponds to VH and VL domain sequences of IL33-158 described in US2018/0037644. Pair 18 corresponds to VH and VL domain sequences of 10C12.38.H6. 87Y.581 lgG4 described in WO2016/077381.

Suitably, the IL-33 binding molecule may competitively inhibit binding of IL-33 to the binding molecule 33_640087-7B (as described in WO2016/156440). Suitably, WO2016/156440 discloses that 33_640087-7B binds to redIL-33 with particularly high affinity and attenuates both ST-2 and RAGE-dependent IL-33 signaling.

Suitably, the IL-33 binding molecule is an anti-IL-33 antibody or antigen-binding fragment thereof comprising the complementarity determining regions (CDRs) of the heavy chain variable region (HCVR) comprising the sequence of SEQ ID NO:1 and the complementarity determining regions (CDRs) of light chain variable region (LCVR) comprising the sequence of SEQ ID NO:19. These CDRs correspond to those derived from 33_640087-7B (as described in WO2016/156440), which binds reduced IL-33 and inhibits its conversion to oxidised IL-33. 33_640087-7B is described in full in WO2016/156440, which is incorporated by reference herein. Thus, this antibody may be particularly useful in the methods described herein to inhibit or attenuate both ST-2 and RAGE signaling.

Suitably the skilled person knows of available methods in the art to identify CDRs within the heavy and light variable regions of an antibody or antigen-binding fragment thereof. Suitably the skilled person may conduct sequence-based annotation, for example. The regions between CDRs are generally highly conserved, and therefore, logic rules can be used to determine CDR location. The skilled person may use a set of sequence-based rules for conventional antibodies (Pantazes and Maranas, Protein Engineering, Design and Selection, 2010), alternatively or additionally he may refine the rules based on a multiple sequence alignment. Alternatively, the skilled person may compare the antibody sequences to a publicly available database operating on Kabat, Chothia or IMGT methods using the BLASTP command of BLAST+ to identify the most similar annotated sequence. Each of these methods has devised a unique residue numbering scheme according to which it numbers the hypervariable region residues and the beginning and ending of each of the six CDRs is then determined according to certain key positions. Upon alignment with the most similar annotated sequence, for example, the CDRs can be extrapolated from the annotated sequence to the non-annotated sequence, thereby identifying the CDRs. Suitable tools/databases are: the Kabat database, Kabatman, Scalinger, IMGT, Abnum for example.

Suitably, the binding molecule is an IL-33 antibody or antigen-binding fragment comprising a variable heavy domain (VH) and variable light domain (VL) pair selected from Table 1.

Suitably, the IL-33 antibody or antigen binding fragment therefore comprises a VH domain of the sequence of SEQ ID NO:1 and a VL domain of the sequence of SEQ ID NO: 19.

Suitably, the IL-33 antibody or antigen binding fragment therefore comprises a VH domain of the sequence of SEQ ID NO:7 and a VL domain of the sequence of SEQ ID NO:25.

Suitably, the IL-33 antibody or antigen binding fragment therefore comprises a VH domain of the sequence of SEQ ID NO:11 and a VL domain of the sequence of SEQ ID NO:29.

Suitably, the IL-33 antibody or antigen binding fragment therefore comprises a VH domain of the sequence of SEQ ID NO: 13 and a VL domain of the sequence of SEQ ID NO:31.

Suitably, the IL-33 antibody or antigen binding fragment therefore comprises a VH domain of the sequence of SEQ ID NO: 16 and a VL domain of the sequence of SEQ ID NO:34.

Suitably, the IL-33 antibody or antigen binding fragment therefore comprises a VH domain of the sequence of SEQ ID NO: 17 and a VL domain of the sequence of SEQ ID NO:35.

Suitably, the IL-33 antibody or antigen binding fragment therefore comprises a VH domain of the sequence of SEQ ID NO: 18 and a VL domain of the sequence of SEQ ID NO:36.

Suitably, the IL-33 antibody or antigen binding fragment comprises a variable heavy chain comprising the 3 CDRs derived from a heavy chain variable region independently selected from SEQ ID NO: 1, 7, 11, 13, 16, 17 and 18.

Suitably the IL-33 antibody or antigen binding fragment thereof comprises a heavy chain variable region comprising the 3 CDRs of the heavy chain variable region according to SEQ ID NO: 1.

Suitably, the IL-33 antibody or antigen binding fragment comprises a light chain variable region comprising the 3 CDRs in a light chain variable region independently selected from SEQ ID NO: 19, 25, 29, 31, 34, 35 and 36.

Suitably, the IL-33 antibody or antigen binding fragment thereof comprises a light chain variable region comprising 3 CDRs in a light chain variable region according to SEQ ID NO: 19.

Suitably, therefore, the IL-33 antibody or antigen binding fragment thereof comprises a heavy chain variable region comprising the 3 CDRs of the heavy chain variable region independently selected from SEQ ID NO: 1, 7, 11, 13, 16, 17 and 18 and comprises a light chain variable region comprising the 3 CDRs in a light chain variable region independently selected from SEQ ID NO: 19, 25, 29, 31, 34, 35 and 36.

Suitably, therefore, the IL-33 antibody or antigen binding fragment thereof comprises a heavy chain variable region comprising the 3 CDRs of the heavy chain variable region according to SEQ ID NO: 1 and comprises a light chain variable region comprising the 3 CDRs in the light chain variable region according to SEQ ID NO: 19.

Suitably, the IL-33 antibody or antigen binding fragment thereof comprises a variable heavy domain (VH) and a variable light domain (VL) having VH CDRs 1-3 having the sequences of SEQ ID NO: 37, 38 and 39, respectively, wherein one or more VHCDRs have 3 or fewer single amino acid substitutions, insertions and/or deletions.

Suitably, the IL-33 antibody or antigen binding fragment thereof comprises a VH domain which comprises VHCDRs 1-3 of SEQ ID NO: 37, SEQ ID NO: 38 and SEQ ID NO: 39, respectively.

Suitably, the IL-33 antibody or antigen binding fragment thereof comprises a VH domain which comprises VHCDRs 1-3 consisting of SEQ ID NO: 37, SEQ ID NO: 38 and SEQ ID NO: 39, respectively.

Suitably, the IL-33 antibody or antigen binding fragment thereof comprises a variable heavy domain (VH) and a variable light domain (VL) having VL CDRs 1-3 having the sequences of SEQ ID NO: 40, 41 and 42, respectively, wherein one or more VLCDRs have 3 or fewer single amino acid substitutions, insertions and/or deletions.

Suitably, the IL-33 antibody or antigen binding fragment thereof comprises a VL domain which comprises VLCDRs 1-3 of SEQ ID NO: 40, SEQ ID NO: 41 and SEQ ID NO: 42, respectively.

Suitably, the IL-33 antibody or antigen binding fragment thereof comprises a VL domain which comprises VLCDRs 1-3 consisting of SEQ ID NO: 40, SEQ ID NO: 41 and SEQ ID NO: 42, respectively.

Suitably, therefore, the IL-33 antibody or antigen binding fragment thereof comprises a VHCDR1 having the sequence of SEQ ID NO: 37, a VHCDR2 having the sequence of SEQ ID NO: 38, a VHCDR3 having the sequence of SEQ ID NO: 39, a VLCDR1 having the sequence of SEQ ID NO: 40, a VLCDR2 having the sequence of SEQ ID NO: 41, and a VLCDR3 having the sequence of SEQ ID NO: 42.

Suitably, the IL-33 antibody or antigen binding fragment thereof comprises a VH and VL, wherein the VH has an amino acid sequence at least 90%, for example 91, 92, 93, 94, 95, 96, 97, 98, 99 or 100% identical to a VH according to SEQ ID NO: 1, 7, 11, 13, 16, 17 and 18.

Suitably, the IL-33 antibody or antigen binding fragment thereof comprises a VH and VL, wherein the VH has an amino acid sequence at least 90%, for example 91, 92, 93, 94, 95, 96, 97, 98, 99 or 100% identical to a VH according to SEQ ID NO: 1.

Suitably, the IL-33 antibody or antigen binding fragment thereof comprises a VH and VL, wherein a VH disclosed above, has a sequence with 1, 2, 3 or 4 amino acids in the framework deleted, inserted and/or independently replaced with a different amino acid.

Suitably, the IL-33 antibody or antigen binding fragment thereof comprises a VH and VL, wherein the VL has an amino acid sequence at least 90%, for example 91, 92, 93, 94, 95, 96, 97, 98, 99 or 100% identical to a VL according to SEQ ID NO: 19, 25, 29, 31, 34, 35 and 36.

Suitably, the IL-33 antibody or antigen binding fragment thereof comprises a VH and VL, wherein the VL has an amino acid sequence at least 90%, for example 91, 92, 93, 94, 95, 96, 97, 98, 99 or 100% identical to a VL according to SEQ ID NO: 19.

Suitably the IL-33 antibody or antigen binding fragment thereof comprises a VH and VL, wherein a VL disclosed above has a sequence with 1, 2, 3 or 4 amino acids in the framework independently deleted, inserted and/or replaced with a different amino acid.

Suitably, the IL-33 antibody or antigen binding fragment thereof comprises a VH and VL, wherein the VH has an amino acid sequence at least 90%, for example 91, 92, 93, 94, 95, 96, 97, 98, 99 or 100% identical to a VH according to SEQ ID NO: 1, 7, 11, 13, 16, 17 and 18, and VL has an amino acid sequence at least 90%, for example 91, 92, 93, 94, 95, 96, 97, 98, 99 or 100% identical to a VL according to SEQ ID NO: 19, 25, 29, 31, 34, 35 and 36.

Suitably, the IL-33 antibody or antigen binding fragment thereof comprises a VH and VL, wherein the VH has an amino acid sequence consisting of SEQ ID NO: 1, 7, 11, 13, 16, 17 and 18, and the VL has an amino acid sequence consisting of SEQ ID NO: 19, 25, 29, 31, 34, 35 and 36.

Suitably, the IL-33 antibody or antigen binding fragment thereof comprises a VH and VL, wherein the VH has an amino acid sequence consisting of SEQ ID NO: 1, and the VL has an amino acid sequence consisting of SEQ ID NO: 19.

Compositions and Administration

The IL-33 antagonists in the medical uses and methods described herein may be administered to a patient in the form of a pharmaceutical composition.

Suitably, any references herein to 'a/the IL-33 antagonist' may also refer to a pharmaceutical composition comprising an/the IL-33 antagonist. Suitably the pharmaceutical composition may comprise one or more IL-33 antagonists.

Suitably the IL-33 antagonist may be administered in a pharmaceutically effective amount for the in vivo treatment of coronavirus disease 2019 (COVID-19), SARS-CoV-2 infection, and/or symptoms thereof.

Suitably a 'pharmaceutically effective amount' or 'therapeutically effective amount' of an IL-33 antagonist shall be held to mean an amount sufficient to achieve effective binding to IL-33 and to achieve a benefit, e.g. to ameliorate symptoms of a disease or condition as recited in the medical uses/methods herein.

Suitably, the IL-33 antagonist or a pharmaceutical composition thereof may be administered to a human or other animal in accordance with the aforementioned methods of treatment/medical uses in an amount sufficient to produce a therapeutic effect.

Suitably, the IL-33 antagonist or a pharmaceutical composition thereof can be administered to such human or other animal in a conventional dosage form prepared by combining the IL-33 antagonist with a conventional pharmaceutically acceptable carrier or diluent according to known techniques.

It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of IL-33 antagonists may prove to be particularly effective.

The amount of IL-33 antagonist that may be combined with the carrier materials to produce a single dosage form will vary depending upon the subject treated and the particular mode of administration.

Suitably, the pharmaceutical composition may be administered as a single dose, multiple doses or over an established period of time in an infusion. Suitably, dosage regimens also may be adjusted to provide the optimum desired response (e.g., a therapeutic or prophylactic response).

Suitably, the IL-33 antagonist will be formulated so as to facilitate administration and promote stability of the IL-33 antagonist.

Suitably, pharmaceutical compositions are formulated to comprise a pharmaceutically acceptable, non-toxic, sterile carrier such as physiological saline, non-toxic buffers, preservatives and the like.

Suitably the pharmaceutical composition may comprise pharmaceutically acceptable carriers, sterile aqueous or non-aqueous solutions, suspensions, and/or emulsions.

Suitably, pharmaceutical compositions for injectable use may include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will be preserved against the contaminating action of microorganisms, such as bacteria and fungi.

Suitable formulations for use in the therapeutic methods disclosed herein are described in Remington's Pharmaceutical Sciences (Mack Publishing Co.) 16th ed. (1980).

Suitably, prevention of the action of microorganisms can be achieved by various antibacterial and antifungal agents. In many cases, it will be suitable to include isotonic agents, in the pharmaceutical composition. Prolonged absorption of the injectable compositions can be brought about by including in the composition an agent which delays absorption.

Suitably, sterile injectable solutions can be prepared by incorporating an IL-33 axis binding antagonist in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the methods of preparation may be vacuum drying and freeze-drying, which yields a powder of an active ingredient plus any additional desired ingredient from a previously sterile-filtered solution thereof.

Methods of administering the IL-33 antagonist or a pharmaceutical composition thereof to a subject in need thereof may be readily determined by those skilled in the art.

Suitably, the route of administration of the IL-33 axis binding antagonist or pharmaceutical composition thereof may be, for example, oral, parenteral, by inhalation or topical. Suitably, the term parenteral as used herein includes, e.g., intravenous, intraarterial, intraperitoneal, intramuscular, subcutaneous, rectal, or vaginal administration.

Suitably, the IL-33 antagonist or pharmaceutical composition thereof may be orally administered in an acceptable dosage form including, e.g., capsules, tablets, aqueous suspensions or solutions.

Suitably, parenteral formulations may be a single bolus dose, an infusion or a loading bolus dose followed with a maintenance dose. These compositions may be administered at specific fixed or variable intervals, e.g., once a day, or on an "as needed" basis.

Suitably, the components as recited hereinabove for preparing a pharmaceutical composition described herein may be packaged and sold in the form of a kit. Such a kit will suitably have labels or package inserts indicating that the associated pharmaceutical compositions are useful for treating a subject suffering from, or predisposed to a disease or disorder.

EXAMPLE

Example 1

Respiratory viral infections are associated with 80% of asthma exacerbation episodes. These exacerbations have high healthcare costs, cause morbidity and, in some cases, even death. Therefore, novel therapeutic tools are needed to alleviate viral exacerbations and the resulting inflammation. The first step towards an improved treatment is to understand the mechanism of viral airway inflammation. A novel lung air-liquid interface (ALI) co-culture system has been developed to understand the crosstalk between epithelium and group 2 innate lymphoid cells (ILC2s) during a viral infection. Located within the lung mucosa they rapidly respond to alarmin cytokines (IL-33, TSLP and IL-25) released by damaged epithelium. ILC2s are front-line immune cells which play a crucial role in driving inflammatory responses. Their activity has been linked to the pathophysiology of ARDS.

In this model system a drug candidate molecule with anti-IL-33 activity was able to prevent ILC2 activation driven by an infected epithelia.

Methods

Primary bronchial epithelial cells (Lonza) were seeded onto 0.4 μm pore polyester membranes in 24-well plates, left submerged in media for 7 days and then air-lifted. This promoted basal cells to differentiate into goblet and ciliated cells. Cultures were maintained for 21 days before viral infection.

ILC2s were isolated from peripheral blood mononuclear cells by positive selection of CD161 expressing cells and sorted by flow cytometry for CD127+, CRTH2+ and c-KIT+/− cells.

qPCR analysis—ALIs were lysed into TRI Reagent® and mRNA was purified using spin columns. TaqMan probes were used to analyse cxcl10 and cc126 expression with gapdh serving as a housekeeper.

Cytokine analysis—supematants were collected from the basolateral region of the ALI cultures and analysed for IP10 (1:20 dilution) and IL-5 (1:4 dilution) secretion using DuoSet® ELISAs from R&D systems.

ALIs were differentiated over 28 days, infected with human rhinovirus-A (HRV-A) for 2 hours on the apical side where the virus enters via ciliated cells. ILC2s isolated from human leukocyte cones are then added in the basolateral region of the ALI cultures and these are incubated for 4-7 days.

Results

Figure 1B:
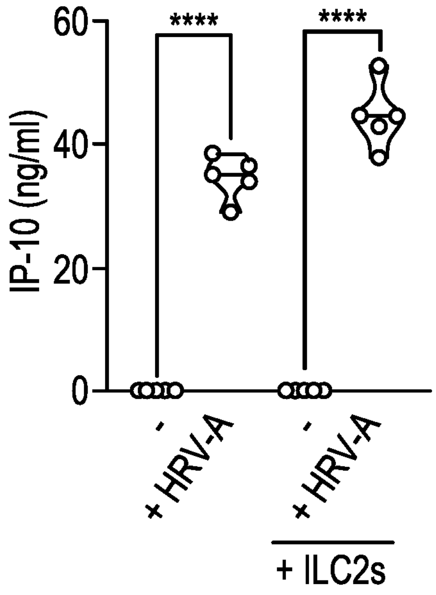
FIG. 1B shows a significant increase in secretion of the viral-response protein IP-10 in ALIs infected with HRV-A and incubated alone or with ILC2s for 7 days (Donors n=5).

ALIs were infected+/−HRV-A and then incubated alone or with ILC2s for 7 days. Viral infection was evaluated by looking at up-regulation of the viral response gene cxcl10 and secretion of the viral-response protein IP-10. There was a significant increase in cxcl10 mRNA and IP-10 release following HRV-A infection. Responses were not altered by incubating ALIs with ILC2s alone (Donors n=5) (FIGS. 1A and 1B).

Figure 1C:
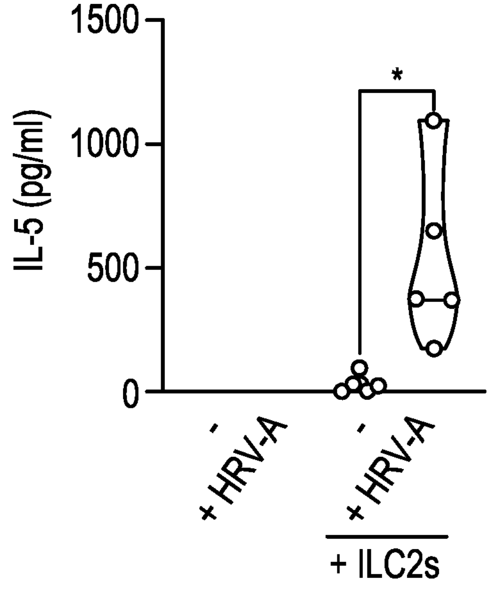
FIG. 1C shows ALIs infected with HRV-A activated ILC2s and induced their secretion of IL-5
Figure 1D:
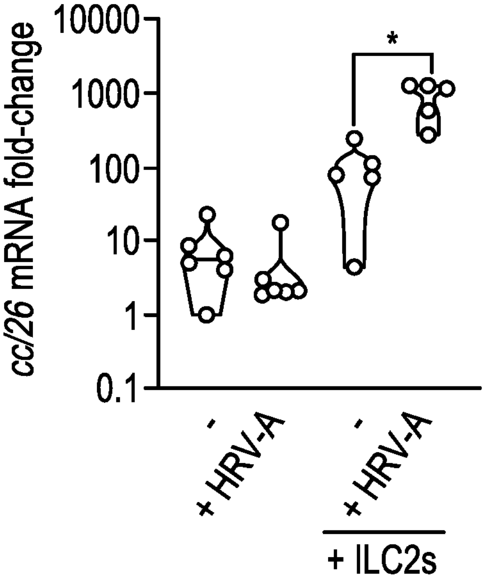
FIG. 1D shows activated ILC2s released cytokines act on ALI cultures to significantly up-regulate the expression of ccl26 (Donors n=5)

The infected ALIs secreted alarmin cytokines which activated ILC2s and induced their secretion of IL-5 (FIG. 1C). Subsequently, activated ILC2s released cytokines which acted on ALI cultures to significantly up-regulate the expression of cc126, a chemotactic for eosinophils and basophils (FIG. 1D). (Donors n=5)

Figure 1E:
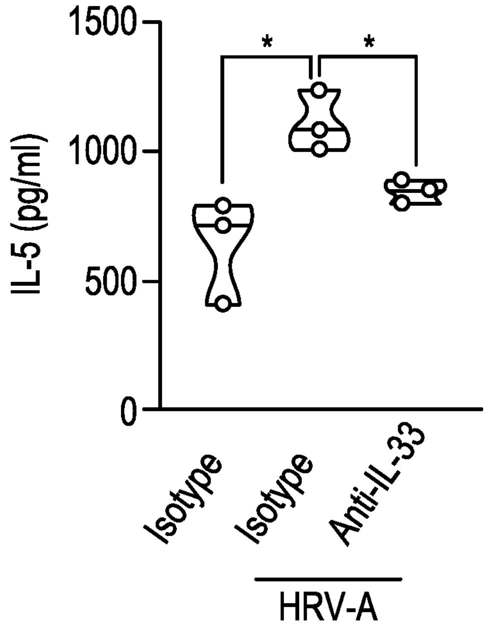
FIG. 1E shows ALIs infected with HRV-A and then incubated with ILC2s and anti-alarmin agents or isotype controls prevented IL-5 secretion from ILC2s

Infected ALIs were also incubated with ILC2s and an IL-33 binding antagonist. The IL-33 axis binding antagonist inhibited HRV-A-infected ALI-induced IL-5 secretion from ILC2s (FIG. 1E). This indicates that IL-33 axis binding antagonists may be useful to prevent ILC2 activation, and may therefore be useful in the prevention or treatment of inflammation in the lung, and conditions associated therewith, such as ARDS.

Example 2

The amount of IL-33 in serum was measured in 100 COVID-positive serum samples from 100 human donors consented on the study entitled: "Evaluating the clinical impact of routine molecular point-of-care testing for COVID-19 in adults presenting to hospital: A prospective, interventional, non-randomized pre and post implementation study (CoV-19POC)"; REC reference: 20/SC/0138; IRAS project ID: 280621.

The free, reduced form of IL-33 (redIL-33) and the IL-33-sST2 complex (IL-33/sST2) were measured in specific immunoassays. Samples analyses were performed using custom S-PLEX assays (MSD) using isoform-specific IL-33 monoclonal antibodies developed in-house by AstraZeneca that enable a lower limit of detection in the fg/ml range. Samples were analysed in duplicate.

Figure 2A:
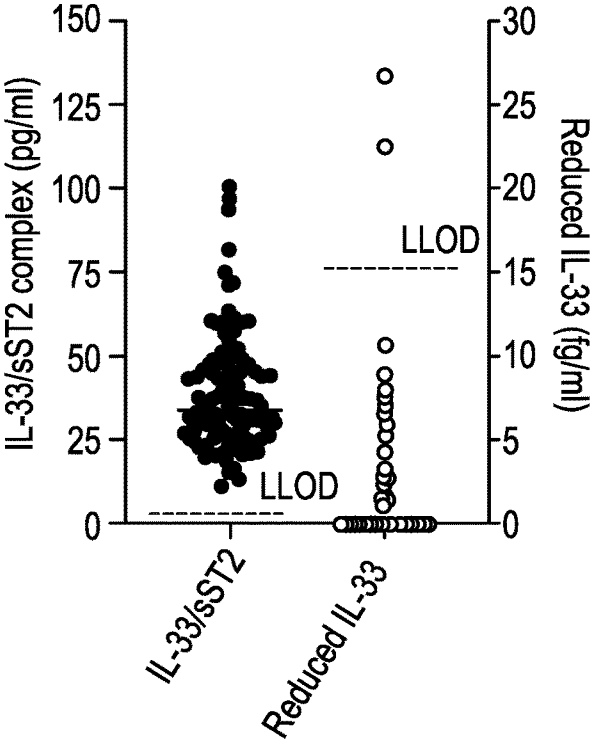
FIG. 2A shows the levels of IL-33 (redIL-33/sST2 complex) and the free, reduced form of IL-33 (reduced IL-33) measured from serum samples obtained from COVID-19-positive humans
Figure 2B:
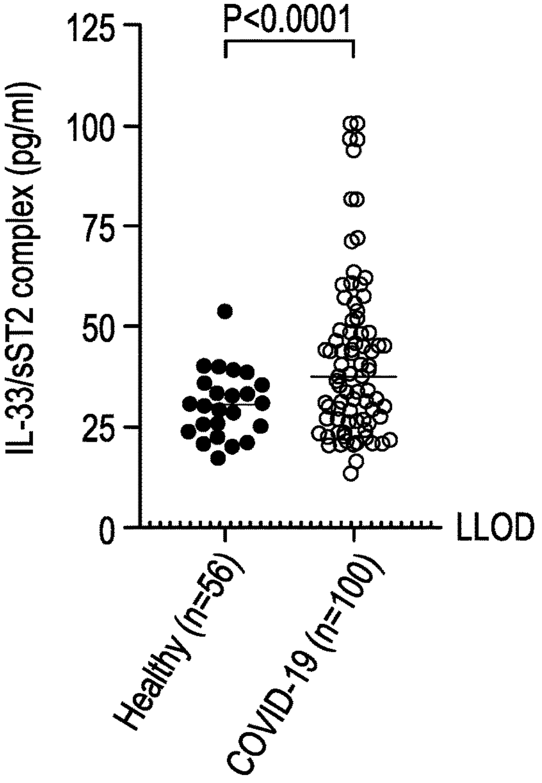
FIG. 2B shows the levels of IL-33/sST2 complex in serum samples obtained from COVID-19-positive humans and healthy subject controls

Results, displayed in FIG. 2A, show IL-33/sST2 and redIL-33 levels in COVID-19 samples. FIG. 2B shows that IL-33/sST2 complex levels are significantly increased in COVID-19-positive serum samples compared to healthy serum controls.

Example 3

A Phase II study is conducted to evaluate the safety and efficacy of adding MEDI3506 to best supportive care for the treatment of COVID-19. MEDI3506 (also disclosed herein as 33_640087-7B) is a fully-human monoclonal antibody that neutralises IL33. IL33 is a broad-acting damage-response cytokine that is released in response to viral infections and tissue damage. Best supportive care is determined by the treating physicians and international guidelines. The study patients are adults (≥18 years) with SARS-CoV-2 infection confirmed by laboratory tests and/or point of care tests and having a score of Grade 3 to 5 on the 9-point ordinal scale:

WHO's 9 Point Category Ordinal Scale:

0. Uninfected, no clinical or biological evidence of infection
1. Not hospitalised, no limitations on activities
2. Not hospitalised, limitation on activities
3. Hospitalised, not requiring supplemental oxygen
4. Hospitalised, requiring supplemental oxygen
5. Hospitalised, on non-invasive ventilation or high flow oxygen devices
6. Hospitalised, intubation and mechanical ventilation
7. Hospitalised, ventilation and additional organ support (ECMO)
8. Death Patients do not participate in the study if they meet any of the following criteria:

- Patients who have previously had a score of 6 or 7 on the 9-point ordinal scale.
- Any patient whose interests are not best served by study participation, as determined by a senior attending clinician.
- Known active infection with HIV or hepatitis B or C.
- Stage 4 severe chronic kidney disease or requiring dialysis (ie, estimated glomerular filtration rate <30 mL/min/1.73 $m^2$).
- History of the following cardiac conditions:
  - Myocardial infarction within 3 months prior to the first dose
  - Unstable angina
  - History of clinically significant dysrhythmias (long QT features on electrocardiogram [ECG], sustained bradycardia [≤55 bpm]), left bundle branch block, cardiac pacemaker or ventricular arrhythmia) or history of familial long QT
- Screening 12-lead ECG with a measurable QTc interval according to Fridericia correction (QTcF)>500 ms.
- Anticipated transfer to another hospital that is not a study centre within 72 hours.
- Allergy to any study medication.
- Experimental off-label usage of medicinal products as treatments for COVID-19.
- Patients participating in another clinical study of an investigational medicinal product.
- Active tuberculosis defined as requiring current treatment for tuberculosis Study Procedures The study is conducted in two stages. Stage 1 will evaluate the preliminary safety and efficacy of MEDI3506 as an add-on to the standard of care (SoC). It is expected that up 60 patients will be randomized for the preliminary analysis. Patients will be randomized to receive either SoC or MEDI3506 as an add-on to SoC. Patients will be randomized on Day 1. Patients randomized onto the MEDI3506 arm will be administered MEDI3506 as a single 300 mg IV dose. A second dose of 300 mg IV MEDI3506 will be administered if the patient is invasively ventilated on or before Day 15.

Stage 2 is conducted to provide confirmatory data, to fully evaluate disease outcomes. Stage 2 will also analyse sever adverse events (AEs), overall AEs, disease-released co-infection complications (e.g., pneumonia and septic shock), and overall mortality, in an expansion stage. The number of patients to be enrolled in Stage 2 will be determined by the results of Stage 1.

Results

The primary endpoint will be measured as time to clinical improvement of at least 2 points (from randomization) on the 9-point category ordinal scale, live discharge form hospital, or considered fit for discharge (a score of 0, 1, or 2 on the ordinal scale), whichever comes first, by Day 29.

Secondary endpoints are as follows:

- The proportion of patients not deteriorating according to the ordinal scale by 1, 2, or 3 points on Days 2, 8, 15, 22, and 29.
- Duration (days) of oxygen use and oxygen-free days.
- Duration (days) of ventilation and ventilation-free days.
- Incidence of any form of new ventilation use and duration (days) of new ventilation use.
- Response rate (number and %) by treatment arm at Days 2, 8, 15, and 29.
- Time to live discharge from the hospital.
- Mortality at Days 15, 29, and 60.
- Time from treatment start date to death.
- $SpO_2/FiO_2$, measured daily from randomisation to Day 15, hospital discharge, or death
- Physical examination.

Clinical laboratory examinations.

Vital signs (blood pressure/heart rate/temperature/respiratory rate).

Adverse events.

Duration (days) of ICU and hospitalisation.

NEWS2 assessed daily while hospitalised and on Days 15 and 29.

Exploratory endpoints are as follows:

Qualitative and quantitative polymerase chain reaction (PCR) determination of severe acute respiratory syndrome coronavirus 2 (SARS-CoV-2) in oropharyngeal/nasal swab while hospitalised on Days 1, 3, 5, 8, 11, 15, and (optional) Day 29.

Additional Sequences

SEQ ID NO 37:
SYAMS

SEQ ID NO 38:
GISAIDQSTYYADSVKG

SEQ ID NO 39:
QKFMQLWGGGLRYPFGY

SEQ ID NO 40:
SGEGMGDKYAA

SEQ ID NO 41:
RDTKRPS

SEQ ID NO 42:
GVIQDNTGV

The invention claimed is:

1. A method of treating a patient with acute respiratory distress syndrome (ARDS) caused by severe acute respiratory syndrome coronavirus 2 (SARS-COV-2), comprising administering to the patient an effective amount of an IL-33 axis binding antagonist, wherein the IL-33 axis binding antagonist is an anti-IL-33 antibody, or antigen binding fragment thereof, and wherein the IL-33 axis binding antagonist comprises a VHCDR1 having the sequence of SEQ ID NO: 37, a VHCDR2 having the sequence of SEQ ID NO: 38, a VHCDR3 having the sequence of SEQ ID NO: 39, a VLCDR1 having the sequence of SEQ ID NO: 40, a VLCDR2 having the sequence of SEQ ID NO: 41, and a VLCDR3 having the sequence of SEQ ID NO: 42.

2. The method of claim 1, wherein the patient needs supplemental oxygen.

3. The method of claim 1, wherein the patient has mild hypoxemia: PaO2 (patient's partial pressure of oxygen)=60 to 79 mmHg; moderate hypoxemia: PaO2=40 to 59 mmHg; or severe hypoxemia: PaO2<40 mmHg.

4. A method of treating hypoxemia caused by severe acute respiratory syndrome coronavirus 2 (SARS-COV-2) in a patient, comprising administering to the patient an effective amount of an IL-33 axis binding antagonist, wherein the IL-33 axis binding antagonist is an anti-IL-33 antibody, or antigen binding fragment thereof, and wherein the IL-33 axis binding antagonist comprises a VHCDR1 having the sequence of SEQ ID NO: 37, a VHCDR2 having the sequence of SEQ ID NO: 38, a VHCDR3 having the sequence of SEQ ID NO: 39, a VLCDR1 having the sequence of SEQ ID NO: 40, a VLCDR2 having the sequence of SEQ ID NO: 41, and a VLCDR3 having the sequence of SEQ ID NO: 42.

5. The method of claim 4, wherein the hypoxemia is mild hypoxemia: PaO2 (patient's partial pressure of oxygen)=60 to 79 mmHg; moderate hypoxemia: PaO2=40 to 59 mmHg; or severe hypoxemia: PaO2<40 mmHg.

6. The method of claim 1, wherein the patient has hypercarbia.

7. The method of claim 1, wherein the method reduces or inhibits inflammation in the lung.

8. The method of claim 1, wherein the patient's partial pressure of oxygen is less than 79 mm HG.

9. The method of claim 1, wherein the patient's partial pressure of oxygen is between 60 and 79 mm HG, inclusive.

10. The method of claim 1, wherein the patient's partial pressure of oxygen is less than 60 mm HG.

11. The method of claim 1, wherein the patient is not or has not yet received mechanical ventilation.

12. A method of treating acute respiratory insufficiency induced by severe acute respiratory syndrome coronavirus 2 (SARS-COV-2) infection in a patient, the method comprises administering to the patient an effective amount of an anti-IL33 antibody, or antigen binding fragment thereof, comprising a VHCDR1 having the sequence of SEQ ID NO: 37, a VHCDR2 having the sequence of SEQ ID NO: 38, a VHCDR3 having the sequence of SEQ ID NO: 39, a VLCDR1 having the sequence of SEQ ID NO: 40, a VLCDR2 having the sequence of SEQ ID NO: 41, and a VLCDR3 having the sequence of SEQ ID NO: 42.

13. The method of claim 4, wherein the patient needs supplemental oxygen.

* * * * *

SEQUENCE LISTING

```
<160> NUMBER OF SEQ ID NOS: 42

<210> SEQ ID NO 1
<211> LENGTH: 126
<212> TYPE: PRT
<213> ORGANISM: Artificial Sequence
<220> FEATURE:
<223> OTHER INFORMATION: PAIR 1 VH

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ala Ile Asp Gln Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Lys Phe Met Gln Leu Trp Gly Gly Gly Leu Arg Tyr Pro
            100                 105                 110

Phe Gly Tyr Trp Gly Gln Gly Thr Met Val Thr Val Ser Ser
        115                 120                 125


<210> SEQ ID NO 2
<211> LENGTH: 122
<212> TYPE: PRT
<213> ORGANISM: Artificial Sequence
<220> FEATURE:
<223> OTHER INFORMATION: PAIR 2 VH

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Ala Met Ser Trp Val Arg Gln Ala Pro Gly Lys Gly Leu Glu Leu Val
        35                  40                  45

Ser Asp Leu Arg Thr Ser Gly Gly Ser Thr Tyr Tyr Ala Asp Ser Val
    50                  55                  60
```

```
Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser His Tyr Ser Thr Ser Trp Phe Gly Gly Phe Asp Tyr Trp
            100                 105                 110

Gly Gln Gly Thr Leu Val Thr Val Ser Ser
        115                 120


<210> SEQ ID NO 3
<211> LENGTH: 121
<212> TYPE: PRT
<213> ORGANISM: Artificial Sequence
<220> FEATURE:
<223> OTHER INFORMATION: PAIR 3 VH

<400> SEQUENCE: 3

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Leu Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn His Phe Ser Leu
65                  70                  75                  80

Lys Leu Ser Ser Val Thr Ala Ala Asp Thr Ala Val Tyr Tyr Cys Ala
                85                  90                  95

Arg Ser Gln Tyr Thr Ser Ser Trp Tyr Gly Ser Phe Asp Ile Trp Gly
            100                 105                 110

Gln Gly Thr Met Val Thr Val Ser Ser
        115                 120


<210> SEQ ID NO 4
<211> LENGTH: 122
<212> TYPE: PRT
<213> ORGANISM: Artificial Sequence
<220> FEATURE:
<223> OTHER INFORMATION: PAIR 4 VH

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Ser Tyr
            20                  25                  30

Gly Ile Ser Trp Val Arg Gln Ala Pro Gly Gln Gly Leu Glu Trp Met
        35                  40                  45

Gly Trp Ile Ser Ser His Asn Gly Asn Ser His Tyr Val Gln Lys Phe
    50                  55                  60

Gln Gly Arg Val Ser Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg His Ser Tyr Thr Thr Ser Trp Tyr Gly Gly Phe Asp Tyr Trp
            100                 105                 110

Gly Gln Gly Thr Leu Val Thr Val Ser Ser
        115                 120
```

<210> SEQ ID NO 5
<211> LENGTH: 122
<212> TYPE: PRT
<213> ORGANISM: Artificial Sequence
<220> FEATURE:
<223> OTHER INFORMATION: PAIR 5 VH

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Leu Thr Trp Val Arg Gln Ala Pro Gly Lys Gly Leu Glu Trp Val
        35                  40                  45

Ser Phe Ile Ser Gly Ser Gly Gly Arg Pro Phe Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Ile Tyr Tyr Cys
                85                  90                  95

Ala Lys Ser Leu Tyr Thr Thr Ser Trp Tyr Gly Gly Phe Asp Ser Trp
            100                 105                 110

Gly Gln Gly Thr Leu Val Thr Val Ser Ser
        115                 120
```

<210> SEQ ID NO 6
<211> LENGTH: 122
<212> TYPE: PRT
<213> ORGANISM: Artificial Sequence
<220> FEATURE:
<223> OTHER INFORMATION: PAIR 6 VH

<400> SEQUENCE: 6

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Val Arg Gln Ala Pro Gly Lys Gly Leu Glu Trp Val
        35                  40                  45

Ser Thr Ile Ser Gly Ser Gly Asp Asn Thr Tyr Tyr Ala Asp Ser Val
    50                  55                  60

Gln Gly Arg Phe Thr Ile Ser Arg Gly His Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Thr Tyr Ser Arg Ser Trp Tyr Gly Ala Phe Asp Phe Trp
            100                 105                 110

Gly Gln Gly Thr Met Val Thr Val Ser Ser
        115                 120
```

<210> SEQ ID NO 7
<211> LENGTH: 122
<212> TYPE: PRT
<213> ORGANISM: Artificial Sequence
<220> FEATURE:
<223> OTHER INFORMATION: PAIR 7 VH

<400> SEQUENCE: 7

```
Glu Val Gln Leu Val Glu Ser Gly Gly Asn Leu Glu Gln Pro Gly Gly
1               5                   10                  15

Ser Leu Arg Leu Ser Cys Thr Ala Ser Gly Phe Thr Phe Ser Arg Ser
            20                  25                  30

Ala Met Asn Trp Val Arg Arg Ala Pro Gly Lys Gly Leu Glu Trp Val
        35                  40                  45

Ser Gly Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Ser Ala Glu Asp Thr Ala Ala Tyr Tyr Cys
                85                  90                  95

Ala Lys Asp Ser Tyr Thr Thr Ser Trp Tyr Gly Gly Met Asp Val Trp
            100                 105                 110

Gly His Gly Thr Thr Val Thr Val Ser Ser
        115                 120


<210> SEQ ID NO 8
<211> LENGTH: 116
<212> TYPE: PRT
<213> ORGANISM: Artificial Sequence
<220> FEATURE:
<223> OTHER INFORMATION: PAIR 8 VH

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Val Arg Gln Ala Pro Gly Lys Gly Leu Glu Trp Val
        35                  40                  45

Ser Ser Ile Ser Arg Tyr Ser Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Gly Gly Met Asp Val Trp Gly Gln Gly Thr Leu Val
            100                 105                 110

Thr Val Ser Ser
        115


<210> SEQ ID NO 9
<211> LENGTH: 119
<212> TYPE: PRT
<213> ORGANISM: Artificial Sequence
<220> FEATURE:
<223> OTHER INFORMATION: PAIR 9 VH

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met His Trp Val Arg Gln Ala Pro Gly Lys Gly Leu Glu Trp Val
        35                  40                  45

Ser Ser Ile Ser Ala Arg Ser Arg Tyr His Tyr Tyr Ala Asp Ser Val
    50                  55                  60
```

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Leu Ala Thr Arg His Asn Ala Phe Asp Ile Trp Gly Gln Gly
100 105 110

Thr Leu Val Thr Val Ser Ser
115

<210> SEQ ID NO 10
<211> LENGTH: 119
<212> TYPE: PRT
<213> ORGANISM: Artificial Sequence
<220> FEATURE:
<223> OTHER INFORMATION: PAIR 10 VH

<400> SEQUENCE: 10

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Tyr Met His Trp Val Arg Gln Ala Pro Gly Lys Gly Leu Glu Trp Val
35 40 45

Ser Ser Ile Ser Ala Arg Ser Ser Tyr Ile Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Leu Ala Thr Arg Asn Asn Ala Phe Asp Ile Trp Gly Gln Gly
100 105 110

Thr Leu Val Thr Val Ser Ser
115

<210> SEQ ID NO 11
<211> LENGTH: 119
<212> TYPE: PRT
<213> ORGANISM: Artificial Sequence
<220> FEATURE:
<223> OTHER INFORMATION: PAIR 11 VH

<400> SEQUENCE: 11

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Arg Tyr
20 25 30

Tyr Met His Trp Val Arg Gln Ala Pro Gly Lys Gly Leu Glu Trp Val
35 40 45

Ser Ser Ile Ser Ala Gln Ser Ser His Ile Tyr Tyr Ala Asp Ser Val
50 55 60

Glu Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Leu Ala Thr Arg Gln Asn Ala Phe Asp Ile Trp Gly Gln Gly
100 105 110

Thr Leu Val Thr Val Ser Ser

115

<210> SEQ ID NO 12
<211> LENGTH: 119
<212> TYPE: PRT
<213> ORGANISM: Artificial Sequence
<220> FEATURE:
<223> OTHER INFORMATION: PAIR 12 VH

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met His Trp Val Arg Gln Ala Pro Gly Lys Gly Leu Glu Trp Val
        35                  40                  45

Ser Ser Ile Ser Ala Arg Ser Ser Tyr Leu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Thr Arg His Val Ala Phe Asp Ile Trp Gly Gln Gly
            100                 105                 110

Thr Leu Val Thr Val Ser Ser
        115

<210> SEQ ID NO 13
<211> LENGTH: 139
<212> TYPE: PRT
<213> ORGANISM: Artificial Sequence
<220> FEATURE:
<223> OTHER INFORMATION: PAIR 13 VH

<400> SEQUENCE: 13

Met Arg Ala Trp Ile Phe Phe Leu Leu Cys Leu Ala Gly Arg Ala Leu
1               5                   10                  15

Ala Gln Val Gln Leu Met Gln Ser Gly Ala Glu Val Lys Lys Pro Gly
            20                  25                  30

Ala Ser Val Lys Val Ser Cys Lys Ala Ser Gly Tyr Thr Phe Thr Ser
        35                  40                  45

Tyr Trp Met His Trp Val Arg Gln Ala Pro Gly Gln Gly Leu Glu Trp
    50                  55                  60

Met Gly Thr Ile Tyr Pro Arg Asn Ser Asn Thr Asp Tyr Asn Gln Lys
65                  70                  75                  80

Phe Lys Ala Arg Val Thr Met Thr Arg Asp Thr Ser Thr Ser Thr Val
                85                  90                  95

Tyr Met Glu Leu Ser Ser Leu Arg Ser Glu Asp Thr Ala Val Tyr Tyr
            100                 105                 110

Cys Ala Arg Pro Leu Tyr Tyr Tyr Leu Thr Ser Pro Pro Thr Leu Phe
        115                 120                 125

Trp Gly Gln Gly Thr Leu Val Thr Val Ser Ser
    130                 135

<210> SEQ ID NO 14
<211> LENGTH: 123
<212> TYPE: PRT
<213> ORGANISM: Artificial Sequence
<220> FEATURE:

<223> OTHER INFORMATION: PAIR 14 VH

<400> SEQUENCE: 14

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Leu His Gly Ile Arg Ala Ala Tyr Asp Ala Phe Ile Ile
            100                 105                 110

Trp Gly Gln Gly Thr Leu Val Thr Val Ser Ser
        115                 120

<210> SEQ ID NO 15
<211> LENGTH: 123
<212> TYPE: PRT
<213> ORGANISM: Artificial Sequence
<220> FEATURE:
<223> OTHER INFORMATION: PAIR 15 VH

<400> SEQUENCE: 15

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Phe Ser Phe Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Leu His Gly Ile Arg Ala Ala Tyr Asp Ala Phe Ile Ile
            100                 105                 110

Trp Gly Gln Gly Thr Leu Val Thr Val Ser Ser
        115                 120

<210> SEQ ID NO 16
<211> LENGTH: 123
<212> TYPE: PRT
<213> ORGANISM: Artificial Sequence
<220> FEATURE:
<223> OTHER INFORMATION: PAIR 16 VH

<400> SEQUENCE: 16

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Phe Ser Phe Tyr
            20                  25                  30

Ala Met Ser Trp Val Arg Gln Ala Pro Gly Lys Gly Leu Glu Trp Val

```
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Ile His Gly Ile Arg Ala Ala Tyr Asp Ala Phe Ile Ile
            100                 105                 110

Trp Gly Gln Gly Thr Leu Val Thr Val Ser Ser
        115                 120


<210> SEQ ID NO 17
<211> LENGTH: 121
<212> TYPE: PRT
<213> ORGANISM: Artificial Sequence
<220> FEATURE:
<223> OTHER INFORMATION: PAIR 17 VH

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ala Ile Thr Pro Asn Ala Gly Glu Asp Tyr Tyr Pro Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser
        115                 120


<210> SEQ ID NO 18
<211> LENGTH: 119
<212> TYPE: PRT
<213> ORGANISM: Artificial Sequence
<220> FEATURE:
<223> OTHER INFORMATION: PAIR 18 VH

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ala Thr Ile Ser Gly Gly Lys Thr Phe Thr Asp Tyr Val Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Thr Arg Ala Asn Tyr Gly Asn Trp Phe Phe Glu Val Trp Gly Gln Gly
            100                 105                 110

Thr Leu Val Thr Val Ser Ser
        115


<210> SEQ ID NO 19
<211> LENGTH: 106
<212> TYPE: PRT
<213> ORGANISM: Artificial Sequence
<220> FEATURE:
<223> OTHER INFORMATION: PAIR 1 VL

<400> SEQUENCE: 19

Ser Tyr Val Leu Thr Gln Pro Pro Ser Val Ser Val Ser Pro Gly Gln
1               5                   10                  15

Thr Ala Ser Ile Thr Cys Ser Gly Glu Gly Met Gly Asp Lys Tyr Ala
            20                  25                  30

Ala Trp Tyr Gln Gln Lys Pro Gly Gln Ser Pro Val Leu Val Ile Tyr
        35                  40                  45

Arg Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gly Val Ile Gln Asp Asn Thr Gly Val
                85                  90                  95

Phe Gly Gly Gly Thr Lys Leu Thr Val Leu
            100                 105


<210> SEQ ID NO 20
<211> LENGTH: 107
<212> TYPE: PRT
<213> ORGANISM: Artificial Sequence
<220> FEATURE:
<223> OTHER INFORMATION: PAIR 2 VL

<400> SEQUENCE: 20

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Phe Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Thr Asn Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105


<210> SEQ ID NO 21
<211> LENGTH: 107
<212> TYPE: PRT
<213> ORGANISM: Artificial Sequence
<220> FEATURE:
<223> OTHER INFORMATION: PAIR 3 VL

<400> SEQUENCE: 21

Asp Ile Gln Met Thr Gln Ser Pro Ser Ser Val Ser Ala Ser Val Gly
```

1 5 10 15

Asp Arg Val Thr Ile Thr Cys Arg Ala Ser Gln Gly Ile Ser Thr Trp
20 25 30

Leu Ala Trp Phe Gln Gln Lys Pro Gly Lys Ala Pro Lys Leu Leu Ile
35 40 45

Tyr Ala Ala Ser Thr Leu Gln Gly Gly Val Pro Ser Arg Phe Ser Gly
50 55 60

Ser Gly Ser Gly Pro Glu Phe Thr Leu Thr Ile Ser Ser Leu Gln Pro
65 70 75 80

Glu Asp Phe Ala Thr Tyr Tyr Cys Gln Gln Ala Asn Ser Phe Pro Trp
85 90 95

Thr Phe Gly Gln Gly Thr Lys Val Glu Ile Lys
100 105

<210> SEQ ID NO 22
<211> LENGTH: 107
<212> TYPE: PRT
<213> ORGANISM: Artificial Sequence
<220> FEATURE:
<223> OTHER INFORMATION: PAIR 4 VL

<400> SEQUENCE: 22

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Phe Ser Ser Trp
20 25 30

Leu Ala Trp Tyr Gln Gln Lys Pro Gly Lys Ala Pro Gln Leu Leu Ile
35 40 45

Tyr Ala Ala Ser Ser Leu Gln Ser Gly Val Pro Ser Arg Phe Ser Gly
50 55 60

Ser Gly Ser Gly Ser Asp Phe Thr Leu Thr Ile Ser Ser Leu Gln Pro
65 70 75 80

Glu Asp Phe Ala Thr Tyr Tyr Cys Gln Gln Ala Asn Ser Phe Pro Leu
85 90 95

Thr Phe Gly Gly Gly Thr Lys Val Glu Ile Lys
100 105

<210> SEQ ID NO 23
<211> LENGTH: 107
<212> TYPE: PRT
<213> ORGANISM: Artificial Sequence
<220> FEATURE:
<223> OTHER INFORMATION: PAIR 5 VL

<400> SEQUENCE: 23

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Val Val Ser Trp
20 25 30

Leu Ala Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Asn Ser Phe Pro Phe
85 90 95

```
Thr Leu Gly Pro Gly Thr Lys Val Asp Ile Lys
            100                 105


<210> SEQ ID NO 24
<211> LENGTH: 107
<212> TYPE: PRT
<213> ORGANISM: Artificial Sequence
<220> FEATURE:
<223> OTHER INFORMATION: PAIR 6 VL

<400> SEQUENCE: 24

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Gln Leu Leu Ile
        35                  40                  45

Tyr Ala Ala Ser Arg Leu Gln Ser Gly Val Pro Ser Arg Phe Trp Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Asn Phe Pro Phe
                85                  90                  95

Thr Phe Gly Pro Gly Thr Lys Val Asp Ile Lys
            100                 105


<210> SEQ ID NO 25
<211> LENGTH: 107
<212> TYPE: PRT
<213> ORGANISM: Artificial Sequence
<220> FEATURE:
<223> OTHER INFORMATION: PAIR 7 VL

<400> SEQUENCE: 25

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Phe Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Gln Gln Ala Asn Ser Val Pro Ile
                85                  90                  95

Thr Phe Gly Gln Gly Thr Arg Leu Glu Ile Lys
            100                 105


<210> SEQ ID NO 26
<211> LENGTH: 109
<212> TYPE: PRT
<213> ORGANISM: Artificial Sequence
<220> FEATURE:
<223> OTHER INFORMATION: PAIR 8 VL

<400> SEQUENCE: 26

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Val
```

20 25 30

Tyr Asp Val His Trp Tyr Gln Gln Leu Pro Gly Thr Ala Pro Lys Leu
35 40 45

Leu Ile Tyr Arg Asn Asn Gln Arg Pro Ser Gly Val Pro Asp Arg Phe
50 55 60

Ser Gly Ser Lys Ser Gly Thr Ser Ala Ser Leu Ala Ile Ser Gly Leu
65 70 75 80

Arg Ser Glu Asp Glu Ala Asp Tyr Tyr Cys Gln Thr Tyr Asp Ser Ser
85 90 95

Arg Trp Val Phe Gly Gly Gly Thr Lys Leu Thr Val Leu
100 105

<210> SEQ ID NO 27
<211> LENGTH: 110
<212> TYPE: PRT
<213> ORGANISM: Artificial Sequence
<220> FEATURE:
<223> OTHER INFORMATION: PAIR 9 VL

<400> SEQUENCE: 27

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Asn Asn
20 25 30

Ala Val Ser Trp Tyr Gln Gln Leu Pro Gly Thr Ala Pro Lys Leu Leu
35 40 45

Ile Tyr Ala Ser Asn Met Arg Val Ile Gly Val Pro Asp Arg Phe Ser
50 55 60

Gly Ser Lys Ser Gly Thr Ser Ala Ser Leu Ala Ile Ser Gly Leu Arg
65 70 75 80

Ser Glu Asp Glu Ala Asp Tyr Tyr Cys Gly Ala Trp Asp Asp Ser Gln
85 90 95

Lys Ala Leu Val Phe Gly Gly Gly Thr Lys Leu Thr Val Leu
100 105 110

<210> SEQ ID NO 28
<211> LENGTH: 110
<212> TYPE: PRT
<213> ORGANISM: Artificial Sequence
<220> FEATURE:
<223> OTHER INFORMATION: PAIR 10 VL

<400> SEQUENCE: 28

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Arg Asn
20 25 30

Ala Val Asn Trp Tyr Gln Gln Leu Pro Gly Thr Ala Pro Lys Leu Leu
35 40 45

Ile Tyr Ala Ser Asn Met Arg Val Ser Gly Val Pro Asp Arg Phe Ser
50 55 60

Gly Ser Lys Ser Gly Thr Ser Ala Ser Leu Ala Ile Ser Gly Leu Arg
65 70 75 80

Ser Glu Asp Glu Ala Asp Tyr Tyr Cys Trp Ala Trp Asp Asp Ser Gln
85 90 95

Lys Val Gly Val Phe Gly Gly Gly Thr Lys Leu Thr Val Leu
100 105 110

<210> SEQ ID NO 29
<211> LENGTH: 110
<212> TYPE: PRT
<213> ORGANISM: Artificial Sequence
<220> FEATURE:
<223> OTHER INFORMATION: PAIR 11 VL

<400> SEQUENCE: 29

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Arg Asn
            20                  25                  30

Ala Val Asn Trp Tyr Gln Gln Leu Pro Gly Thr Ala Pro Lys Leu Leu
        35                  40                  45

Ile Tyr Ala Ser Asn Met Arg Arg Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Ala Trp Asp Asp Ser Gln
                85                  90                  95

Lys Val Val Val Phe Gly Gly Gly Thr Lys Leu Thr Val Leu
            100                 105                 110
```

<210> SEQ ID NO 30
<211> LENGTH: 110
<212> TYPE: PRT
<213> ORGANISM: Artificial Sequence
<220> FEATURE:
<223> OTHER INFORMATION: PAIR 12 VL

<400> SEQUENCE: 30

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Ala Ser Asn Met Arg Arg Pro Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Glu Ala Trp Asp Asp Ser Gln
                85                  90                  95

Lys Ala Val Val Phe Gly Gly Gly Thr Lys Leu Thr Val Leu
            100                 105                 110
```

<210> SEQ ID NO 31
<211> LENGTH: 125
<212> TYPE: PRT
<213> ORGANISM: Artificial Sequence
<220> FEATURE:
<223> OTHER INFORMATION: PAIR 13 VL

<400> SEQUENCE: 31

```
Met Arg Ala Trp Ile Phe Phe Leu Leu Cys Leu Ala Gly Arg Ala Leu
1               5                   10                  15

Ala Asp Ile Gln Leu Thr Gln Ser Pro Ser Phe Leu Ser Ala Ser Val
            20                  25                  30

Gly Asp Arg Val Thr Ile Thr Cys Lys Ala Ser Gln Asp Val Gly Thr
```

```
        35                  40                  45

Ala Val Ala Trp Tyr Gln Gln Lys Pro Gly Lys Ala Pro Lys Leu Leu
    50                  55                  60

Ile Tyr Trp Ala Ser Thr Arg His Thr Gly Val Pro Ser Arg Phe Ser
65                  70                  75                  80

Gly Ser Gly Ser Gly Thr Glu Phe Thr Leu Thr Ile Ser Ser Leu Gln
                85                  90                  95

Pro Glu Asp Phe Ala Thr Tyr Tyr Cys Gln Gln Ala Lys Thr Tyr Pro
            100                 105                 110

Phe Thr Phe Gly Ser Gly Thr Lys Leu Glu Ile Lys Arg
        115                 120                 125


<210> SEQ ID NO 32
<211> LENGTH: 108
<212> TYPE: PRT
<213> ORGANISM: Artificial Sequence
<220> FEATURE:
<223> OTHER INFORMATION: PAIR 14 VL

<400> SEQUENCE: 32

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ile Asn
            20                  25                  30

Leu Ser Trp Tyr Gln Gln Lys Pro Gly Gln Ala Pro Arg Leu Leu Ile
        35                  40                  45

Tyr Gly Ala Ser His Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys His Gln Tyr Ser Gln Ser Pro Pro
                85                  90                  95

Phe Thr Phe Gly Gly Gly Thr Lys Val Glu Ile Lys
            100                 105


<210> SEQ ID NO 33
<211> LENGTH: 108
<212> TYPE: PRT
<213> ORGANISM: Artificial Sequence
<220> FEATURE:
<223> OTHER INFORMATION: PAIR 15 VL

<400> SEQUENCE: 33

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ile Asn
            20                  25                  30

Leu Ser Trp Tyr Gln Gln Lys Pro Gly Gln Ala Pro Arg Leu Leu Ile
        35                  40                  45

Tyr Gly Ala Ser His Arg Leu Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys His Gln Tyr Ser Gln Pro Pro Pro
                85                  90                  95

Phe Thr Phe Gly Gly Gly Thr Lys Val Glu Ile Lys
            100                 105
```

<210> SEQ ID NO 34
<211> LENGTH: 108
<212> TYPE: PRT
<213> ORGANISM: Artificial Sequence
<220> FEATURE:
<223> OTHER INFORMATION: PAIR 16 VL

<400> SEQUENCE: 34

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ile Asn
            20                  25                  30

Leu Ser Trp Tyr Gln Gln Lys Pro Gly Gln Ala Pro Arg Leu Leu Ile
        35                  40                  45

Tyr Gly Ala Ser His Arg Leu Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys His Gln Tyr Ser Gln Pro Pro Pro
                85                  90                  95

Phe Thr Phe Gly Gly Gly Thr Lys Val Glu Ile Lys
            100                 105
```

<210> SEQ ID NO 35
<211> LENGTH: 106
<212> TYPE: PRT
<213> ORGANISM: Artificial Sequence
<220> FEATURE:
<223> OTHER INFORMATION: PAIR 17 VL

<400> SEQUENCE: 35

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys His
            20                  25                  30

Leu Asp Trp Tyr Gln Gln Lys Pro Gly Lys Ala Pro Lys Leu Leu Ile
        35                  40                  45

Tyr Phe Thr Asn Asn Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Phe Gln Tyr Asn Gln Gly Trp Thr
                85                  90                  95

Phe Gly Gly Gly Thr Lys Val Glu Ile Lys
            100                 105
```

<210> SEQ ID NO 36
<211> LENGTH: 111
<212> TYPE: PRT
<213> ORGANISM: Artificial Sequence
<220> FEATURE:
<223> OTHER INFORMATION: PAIR 18 VL

<400> SEQUENCE: 36

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ala Lys Tyr
            20                  25                  30

Gly Leu Ser Leu Leu Asn Trp Phe Gln Gln Lys Pro Gly Gln Pro Pro
```

```
        35                  40                  45

Arg Leu Leu Ile Phe Ala Ala Ser Asn Arg Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Val Pro Phe Thr Phe Gly Gln Gly Thr Lys Val Glu Ile Lys
            100                 105                 110


<210> SEQ ID NO 37
<211> LENGTH: 5
<212> TYPE: PRT
<213> ORGANISM: Artificial Sequence
<220> FEATURE:
<223> OTHER INFORMATION: PAIR 1 HCDR1

<400> SEQUENCE: 37

Ser Tyr Ala Met Ser
1               5


<210> SEQ ID NO 38
<211> LENGTH: 17
<212> TYPE: PRT
<213> ORGANISM: Artificial Sequence
<220> FEATURE:
<223> OTHER INFORMATION: PAIR 1 HCDR2

<400> SEQUENCE: 38

Gly Ile Ser Ala Ile Asp Gln Ser Thr Tyr Tyr Ala Asp Ser Val Lys
1               5                   10                  15

Gly


<210> SEQ ID NO 39
<211> LENGTH: 17
<212> TYPE: PRT
<213> ORGANISM: Artificial Sequence
<220> FEATURE:
<223> OTHER INFORMATION: PAIR 1 HCDR3

<400> SEQUENCE: 39

Gln Lys Phe Met Gln Leu Trp Gly Gly Gly Leu Arg Tyr Pro Phe Gly
1               5                   10                  15

Tyr


<210> SEQ ID NO 40
<211> LENGTH: 11
<212> TYPE: PRT
<213> ORGANISM: Artificial Sequence
<220> FEATURE:
<223> OTHER INFORMATION: PAIR 1 LCDR1

<400> SEQUENCE: 40

Ser Gly Glu Gly Met Gly Asp Lys Tyr Ala Ala
1               5                   10


<210> SEQ ID NO 41
<211> LENGTH: 7
<212> TYPE: PRT
<213> ORGANISM: Artificial Sequence
<220> FEATURE:
<223> OTHER INFORMATION: PAIR 1 LCDR2

<400> SEQUENCE: 41
```

-continued

```
Arg Asp Thr Lys Arg Pro Ser
1               5


<210> SEQ ID NO 42
<211> LENGTH: 9
<212> TYPE: PRT
<213> ORGANISM: Artificial Sequence
<220> FEATURE:
<223> OTHER INFORMATION: PAIR 1 LCDR3

<400> SEQUENCE: 42

Gly Val Ile Gln Asp Asn Thr Gly Val
1               5
```